US012729221B2

(12) United States Patent
Yoon et al.

(10) Patent No.: US 12,729,221 B2
(45) Date of Patent: Sep. 8, 2026

(54) ANTI-INFLAMMATORY PEPTIDE AND USE THEREOF

(71) Applicant: MITO QUEST CO., LTD., Seoul (KR)

(72) Inventors: Chang Min Yoon, Yongin-si (KR); Pil Je Park, Seoul (KR)

(73) Assignee: MITO QUEST CO., LTD., Seoul (KR)

( * ) Notice: Subject to any disclaimer, the term of this patent is extended or adjusted under 35 U.S.C. 154(b) by 882 days.

(21) Appl. No.: 17/927,737

(22) PCT Filed: May 28, 2021

(86) PCT No.: PCT/KR2021/006679
§ 371 (c)(1),
(2) Date: Nov. 25, 2022

(87) PCT Pub. No.: WO2021/242046
PCT Pub. Date: Dec. 2, 2021

(65) Prior Publication Data

US 2023/0203097 A1 Jun. 29, 2023

(30) Foreign Application Priority Data

May 28, 2020 (KR) ........................ 10-2020-0064483

(51) Int. Cl.
*C07K 7/06* (2006.01)
*A61K 38/00* (2006.01)
*A61P 29/00* (2006.01)
*C12N 15/62* (2006.01)

(52) U.S. Cl.
CPC ................ *C07K 7/06* (2013.01); *A61P 29/00* (2018.01); *C12N 15/62* (2013.01); *A61K 38/00* (2013.01); *C07K 2319/03* (2013.01)

(58) Field of Classification Search
CPC ........... C07K 7/06; A61P 29/00; C12N 15/62; A61K 38/00
See application file for complete search history.

(56) References Cited

U.S. PATENT DOCUMENTS

| | | | |
|---|---|---|---|
| 5,516,891 | A | 5/1996 | Siwruk et al. |
| 2012/0157395 | A1 | 6/2012 | Ibuki et al. |

FOREIGN PATENT DOCUMENTS

| | | | | |
|---|---|---|---|---|
| JP | 2015522586 A | 8/2015 | | |
| KR | 20110130943 A | 12/2011 | | |
| KR | 101263212 B1 | 5/2013 | | |
| KR | 101510941 B1 | 4/2015 | | |
| WO | WO2011007612 A1 | 1/2011 | | |
| WO | WO-2018068135 A1 * | 4/2018 | .......... | C12N 15/102 |

OTHER PUBLICATIONS

The partial supplementary European search report of 21813743.8, Jul. 2, 2024.

Fraune Johanna et al, Hydra meiosis reveals unexpected conservation of structural synaptonemal complex proteins across metazoans, Proceedings of the National Academy of Sciences, Oct. 9, 2012, vol. 109, No. 41, pp. 16588-16593, PNAS, Washington, D.C., USA.

Koo Ja-Hyun et al, LRR domain of NLRX1 protein delivery by dNP2 inhibits T cell functions and alleviates autoimmune encephalomyelitis, Theranostics, Feb. 10, 2020, vol. 10, No. 7, pp. 3138-3150, Ivyspring International Publisher, Sydney, Australia.

Qi Nan et al, Multiple truncated isoforms of MAVS prevent its spontaneous aggregation in antiviral innate immune signalling, Nature Communications, Aug. 11, 2017, vol. 8, No. 1, pp. 1-16, Nature Communications, London, United Kingdom.

Valentina Armiento et al, Peptide-Based Molecular Strategies to Interfere with Protein Misfolding, Aggregation, and Cell Degeneration, Angewandte Chemie International Edition, Nov. 28, 2019, vol. 59, No. 9, pp. 3372-3384, Wiley-VCH Verlag Gmbh & Co. KGaA, Weinheim, Germany.

International search report of PCT/KR2021/006679, Aug. 30, 2021, English translation.

GenBank: MBP27326.1, Hypothetical protein CMJ63_03795 [Planctomycetaceae bacterium], GenPept, Jul. 13, 2018, Bethesda, USA.

Sara La Manna et al, Peptides as Therapeutic Agents for Inflammatory-Related Diseases, International Journal of Molecular Sciences, Sep. 11, 2018, vol. 19, Issue 2714, pp. 1-18, MDPI, Basel, Switzerland.

Dongkyung Chang et al, Follow-up of Ulcerative Colitis : Short-term Outcome to Medical Treatment and Relpse Rates, Koreanstudies Information Service System, Jan. 1994, pp. 907-918; The Korean Journal of Gastroenterology, Seoul, Republic of Korea, English translation of abstract only.

Charles S Dela Cruz and Min-Jong Kang, Mitochondrial dysfunction and damage associated molecular patterns (DAMPs) in chronic inflammatory diseases, Mitochondrion, Jul. 2018, vol. 41, pp. 37-44, Elsevier, Amsterdam, Netherlands, abstract only.

Heinzmann A and Daser A, Mouse Models for the Genetic Dissection of Atopy, 2002, International Archives of allergy and Immunology, vol. 127, pp. 170-180, Karger, Basel, Switzerland, Abstract only.

(Continued)

*Primary Examiner* — Amber D Steele
(74) *Attorney, Agent, or Firm* — STIP Law Group, LLC

(57) ABSTRACT

The present disclosure relates to an anti-inflammatory peptide including at least one selected from the group consisting of the amino acid sequences of SEQ ID NOS: 1 to 63 and modifications thereof, an anti-inflammatory composition comprising the same, and a pharmaceutical composition for preventing or treating inflammatory diseases. An anti-inflammatory peptide according to an embodiment of the present disclosure has no cytotoxicity, and has an effect of inhibiting the activation of mitochondrial antiviral signaling protein (MAVS), immune/inflammatory activation mechanism and the expression or activity of inflammatory cytokines and inflammasomes. Therefore, the peptide can be applied to an anti-inflammatory composition or a composition for treating inflammatory diseases.

3 Claims, 27 Drawing Sheets

Specification includes a Sequence Listing.

(56) References Cited

OTHER PUBLICATIONS

Sambrook J et al, Molecular cloning: a laboratory manual. 1989, Cold Spring Harbor Laboratory Press, Cold Spring Harbor, USA, Abstract only.
Seon-Young Kim et al, Anti-inflammatory Effect of Stevia Rebaudiana as a Results of NF-κB and MAPK Inhibition, The Journal of Korean Medical Ophthalmology &Otolaryngology & Dermatology, 2013, vol. 26, Issue 3, pp. 54-64, The Society of Korean Medical Ophthalmology & Otolaryngology & Dermatology, Busan, Republic of Korea, English translation of abstract.
R. B. Merrifield, Solid Phase Peptide Synthesis. I. The Synthesis of aTetrapeptide, Journal of American Chemistry Society, Jul. 1, 1963, vol. 85, Issue 14, American Chemical Society, New York, USA, abstract and partial introduction only.
Il-Sung Song et al, Current status of Crohn's disease in Korea, Korean Journal of Medicine, 1998, Korean Journal of Medicine, Seoul, Republic of Korea, abstract only.
Yoon-Young Sung et al, Inhibitory effects of Drynaria fortunei extract on house dust mite antigen-induced atopic dermatitis in NC/Nga mice, Journal of Ethnopharmacology, Oct. 31, 2012, Gol 144, Issue 1, pp. 94-100, Science Direct, Amsterdam, Netherlands.
Tully, B.J et al, MAG: Hypothetical protein CMJ63_03795[Planctomycetaceae bacterium], GenBank: MBP27326.1, 2018, NCBI, Bethesda, MD, USA.
Anantharaman K et al, MAG: Hypothetical protein A2V83_11730 [Nitrospirae bacterim RBG_16_64_22], GenBank: OGW62504.1, 2016, NCBI, Bethesda, MD, USA.
MAG: Planctomycetaceae bacterium isolate NP82 MHASMcontig_353395, whole genome shotgun sequence, GenBank: PBSQ01000070.1, 2018, National Institutes of Health, Bethesda, USA.

* cited by examiner

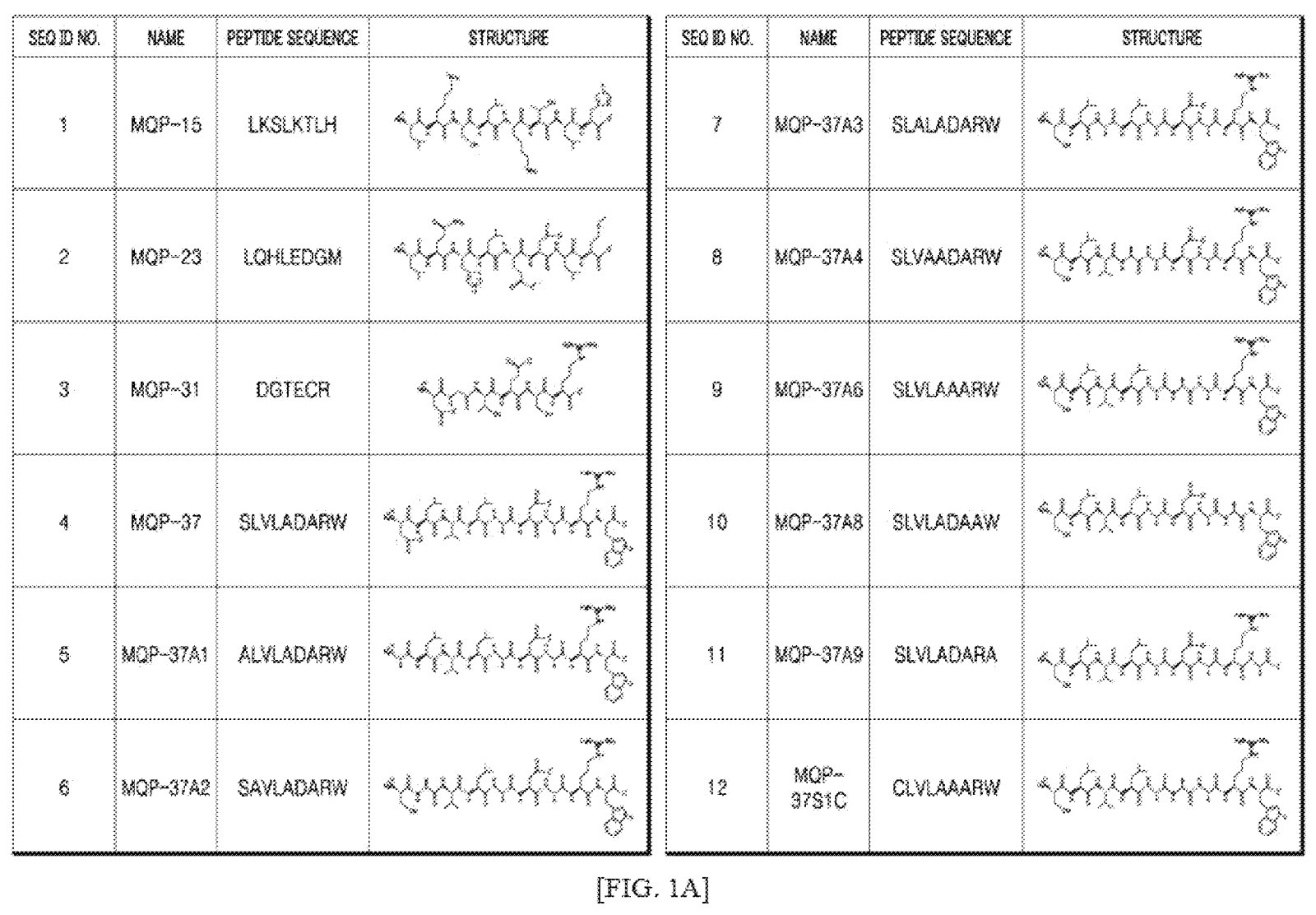

| SEQ ID NO. | NAME | PEPTIDE SEQUENCE | STRUCTURE |
|---|---|---|---|
| 1 | MQP-15 | LKSLKTLH | |
| 2 | MQP-23 | LQHLEDGM | |
| 3 | MQP-31 | DGTECR | |
| 4 | MQP-37 | SLVLADARW | |
| 5 | MQP-37A1 | ALVLADARW | |
| 6 | MQP-37A2 | SAVLADARW | |
| 7 | MQP-37A3 | SLALADARW | |
| 8 | MQP-37A4 | SLVAADARW | |
| 9 | MQP-37A6 | SLVLAAARW | |
| 10 | MQP-37A8 | SLVLADAAW | |
| 11 | MQP-37A9 | SLVLADARA | |
| 12 | MQP-37S1C | CLVLAAARW | |

[FIG. 1A]

| SEQ ID NO. | NAME | PEPTIDE SEQUENCE | STRUCTURE |
|---|---|---|---|
| 13 | MQP-37S1D | DLVLAAARW | |
| 14 | MQP-37S1E | ELVLAAARW | |
| 15 | MQP-37S1F | FLVLAAARW | |
| 16 | MQP-37S1G | GLVLAAARW | |
| 17 | MQP-37S1H | HLVLAAARW | |
| 18 | MQP-37S1I | ILVLAAARW | |

| SEQ ID NO. | NAME | PEPTIDE SEQUENCE | STRUCTURE |
|---|---|---|---|
| 19 | MQP-37S1K | KLVLAAARW | |
| 20 | MQP-37S1L | LLVLAAARW | |
| 21 | MQP-37S1M | MLVLAAARW | |
| 22 | MQP-37S1N | NLVLAAARW | |
| 23 | MQP-37S1P | PLVLAAARW | |
| 24 | MQP-37S1Q | QLVLAAARW | |

[FIG. 1B]

| SEQ ID NO. | NAME | PEPTIDE SEQUENCE | STRUCTURE |
|---|---|---|---|
| 25 | MQP-37S1R | RLVLAAARW | |
| 26 | MQP-37S1T | TLVLAAARW | |
| 27 | MQP-37S1V | VLVLAAARW | |
| 28 | MQP-37S1W | WLVLAAARW | |
| 29 | MQP-37S1Y | YLVLAAARW | |
| 30 | MQP-37D6C | SLVLACARW | |

| SEQ ID NO. | NAME | PEPTIDE SEQUENCE | STRUCTURE |
|---|---|---|---|
| 31 | MQP-37D6E | SLVLAEARW | |
| 32 | MQP-37D6F | SLVLAFARW | |
| 33 | MQP-37D6G | SLVLAGARW | |
| 34 | MQP-37D6H | SLVLAHARW | |
| 35 | MQP-37D6I | SLVLAIARW | |
| 36 | MQP-37D6K | SLVLAKARW | |

[FIG. 1C]

| SEQ ID NO. | NAME | PEPTIDE SEQUENCE | STRUCTURE |
|---|---|---|---|
| 37 | MQP-37D6L | SLVLALARW | |
| 38 | MQP-37D6M | SLVLAMARW | |
| 39 | MQP-37D6N | SLVLANARW | |
| 40 | MQP-37D6P | SLVLAPARW | |
| 41 | MQP-37D6Q | SLVLAQARW | |
| 42 | MQP-37D6R | SLVLARARW | |

| SEQ ID NO. | NAME | PEPTIDE SEQUENCE | STRUCTURE |
|---|---|---|---|
| 43 | MQP-37D6S | SLVLASARW | |
| 44 | MQP-37D6T | SLVLATARW | |
| 45 | MQP-37D6V | SLVLAVARW | |
| 46 | MQP-37D6W | SLVLAWARW | |
| 47 | MQP-37D6Y | SLVLAYARW | |
| 48 | MQP-Y9 | KRLLFWIFIK | |

[FIG. 1D]

| SEQ ID NO. | NAME | PEPTIDE SEQUENCE | STRUCTURE |
|---|---|---|---|
| 49 | MQP-91 | QMVSMVG | |
| 50 | MQP-T234 | KVGDRARWG SRS | |
| 51 | MQP-S442 | LERQSRSWRN | |
| 52 | MQP-341 | EWLGRGRFNG | |
| 53 | MQP-Y9A1 | ARLLFWIFIK | |
| 54 | MQP-Y9A2 | KALLFWIFIK | |
| 55 | MQP-Y9A3 | KRALFWIFIK | |
| 56 | MQP-Y9A4 | KRLAFWIFIK | |
| 57 | MQP-Y9A5 | KRLLAWIFIK | |
| 58 | MQP-Y9A6 | KRLLFAIFIK | |
| 59 | MQP-Y9A7 | KRLLFWAFIK | |
| 60 | MQP-Y9A8 | KRLLFWIAIK | |

[FIG. 1E]

【FIG. 1F】
| SEQ ID NO. | NAME | PEPTIDE SEQUENCE | STRUCTURE |
|---|---|---|---|
| 61 | MQP-Y9A9 | KRLLFWIFAK | |
| 62 | MQP-Y9A10 | KRLLFWIFIA | |
| 63 | MQP-37S1A | ALVLAAARW | |
【FIG. 2】
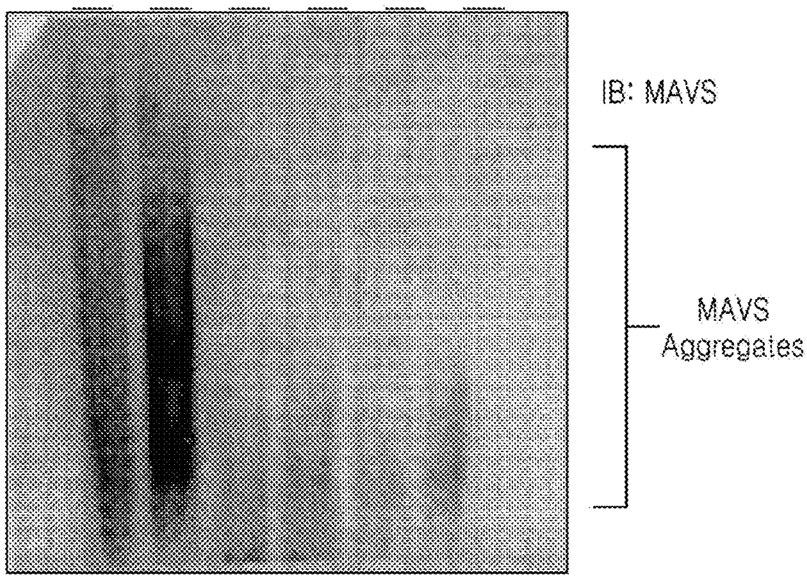

【FIG. 3A】
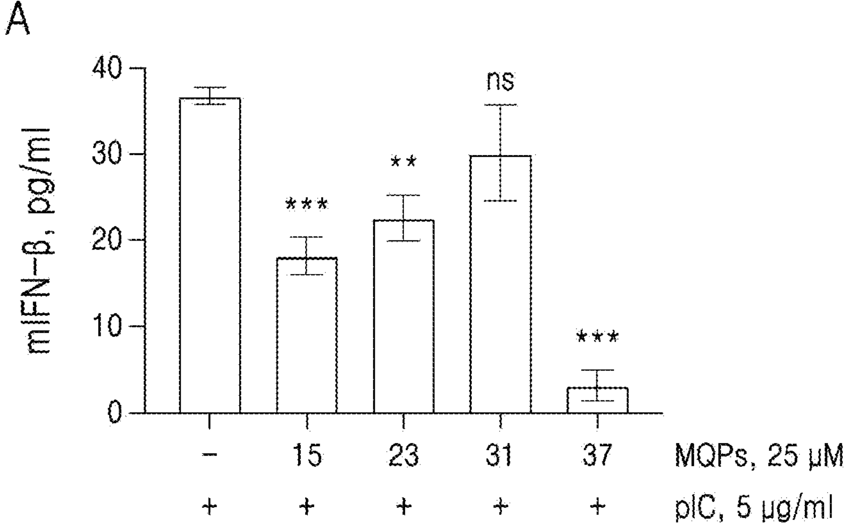
ns, not significant; , P < 0.01; *, P < 0.001
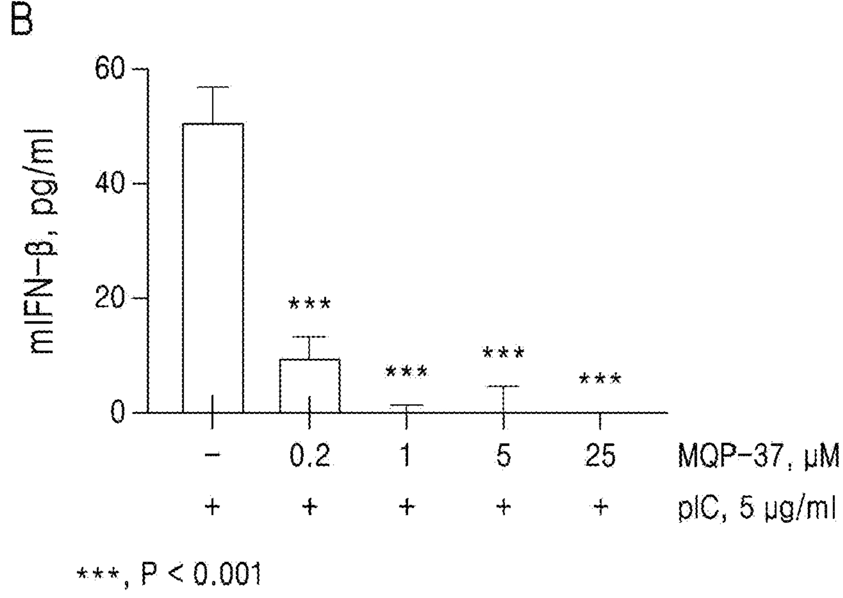
***, P < 0.001

【FIG. 3B】
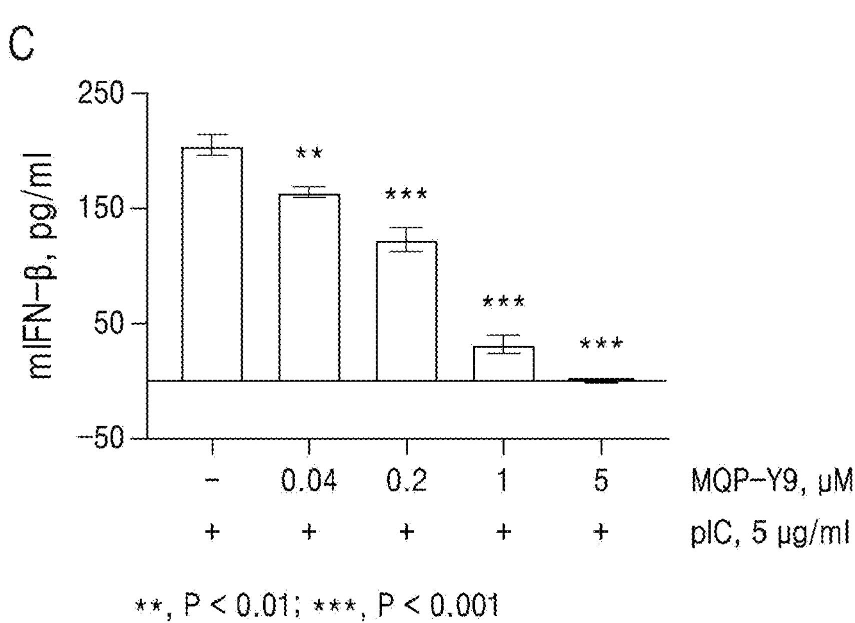
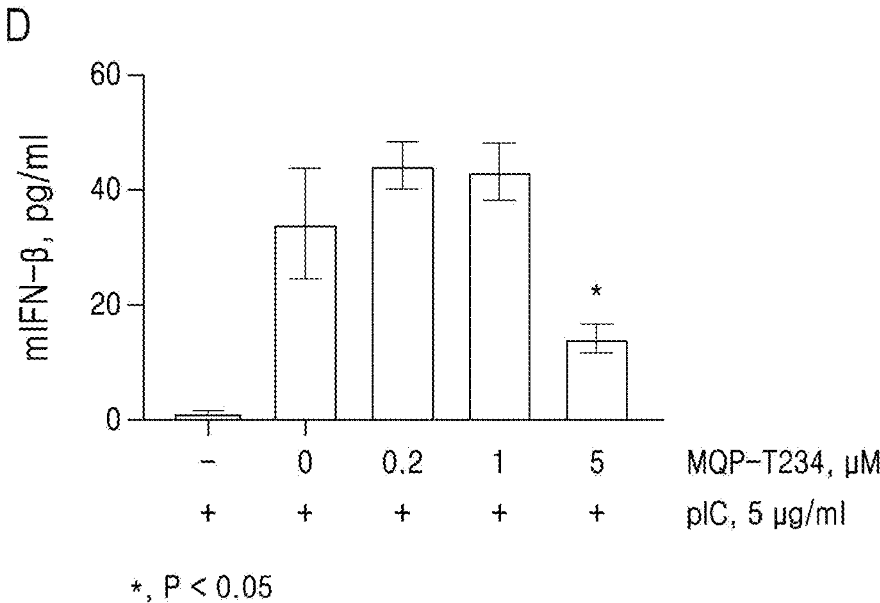

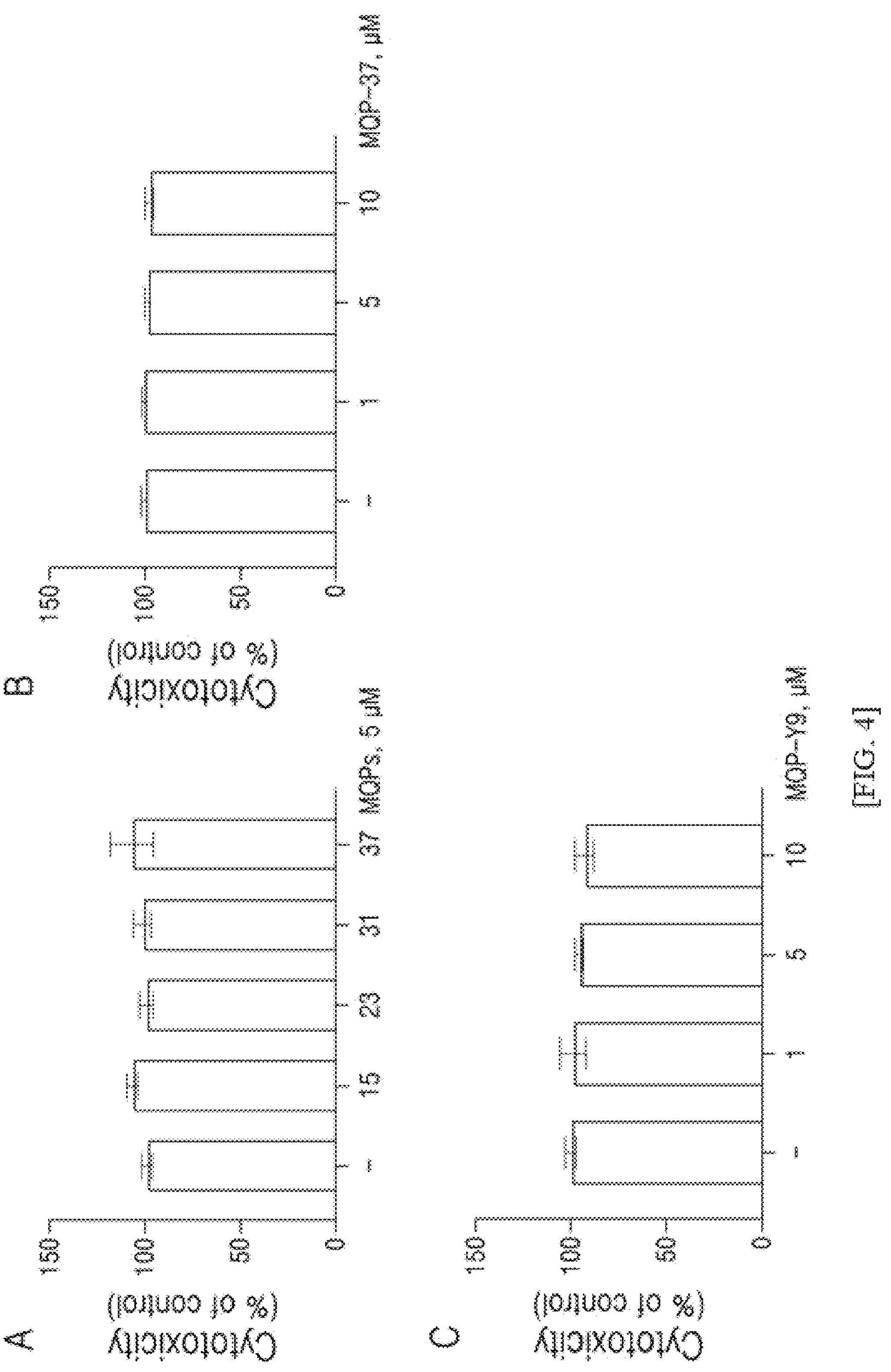
[FIG. 4]

【FIG. 5A】
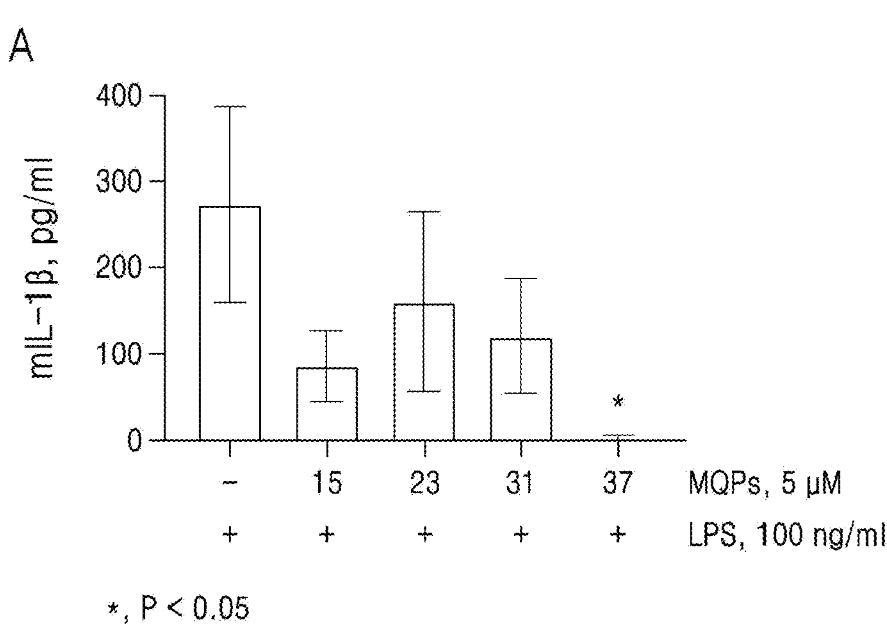
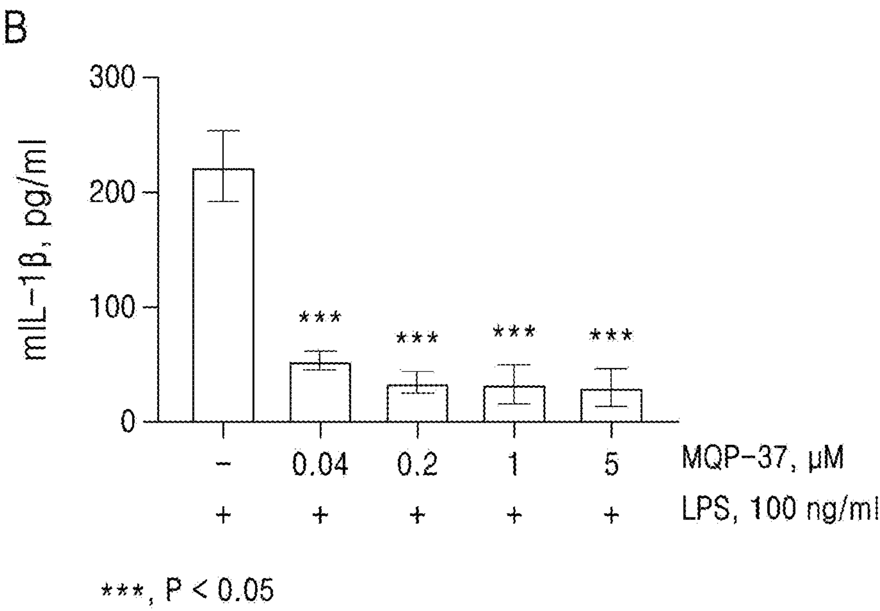

【FIG. 5B】
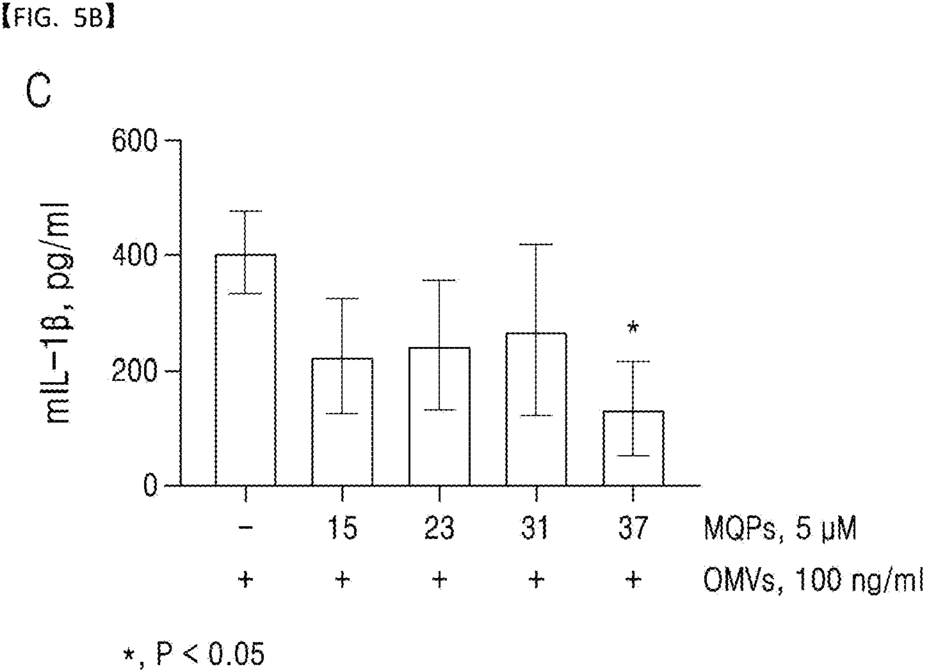
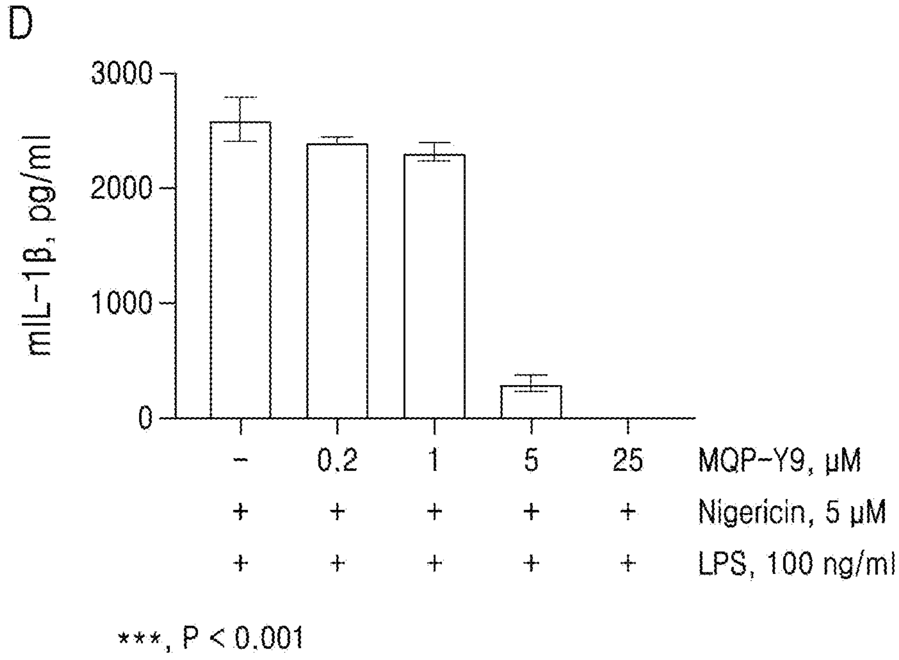

【FIG. 5C】
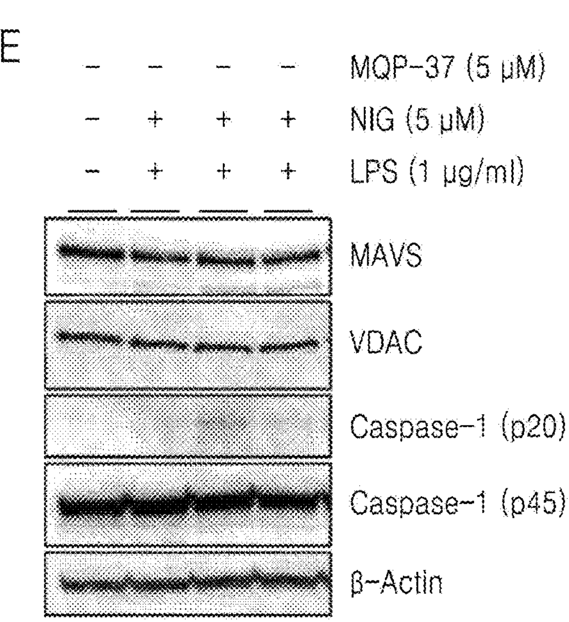

【FIG. 6A】
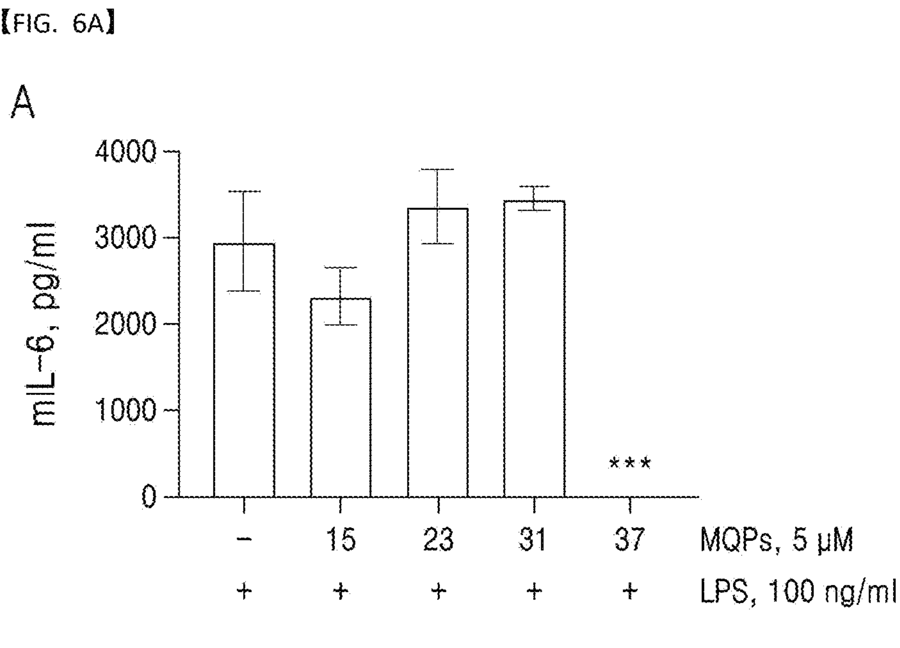
*, P < 0.05
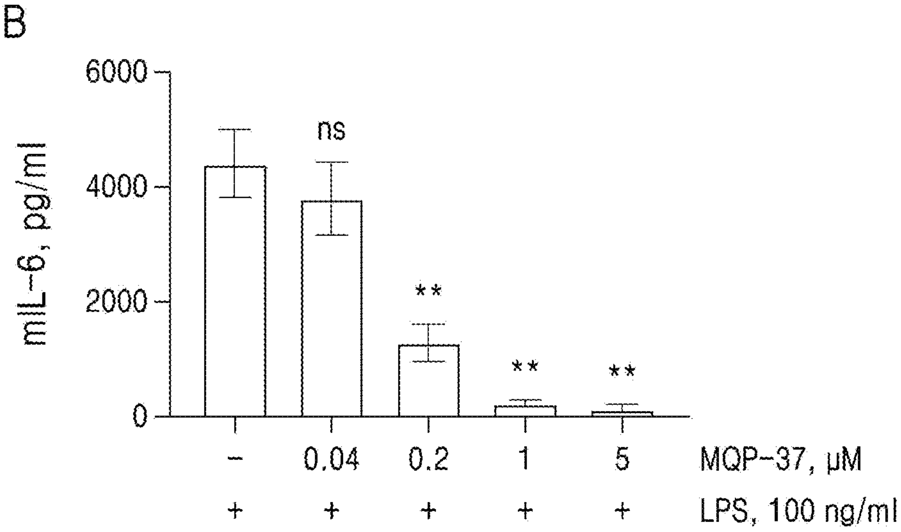
ns, not significant; **, P < 0.01

【FIG. 6B】
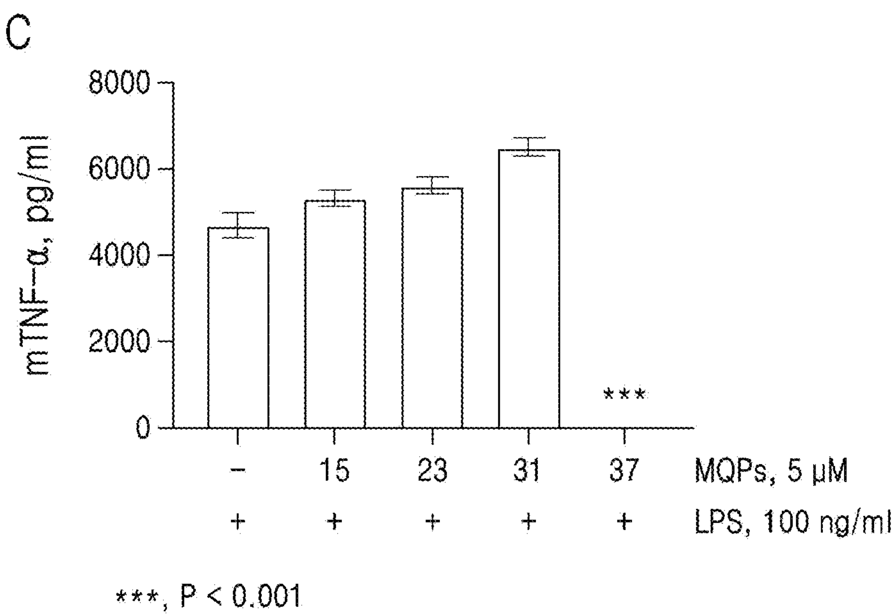
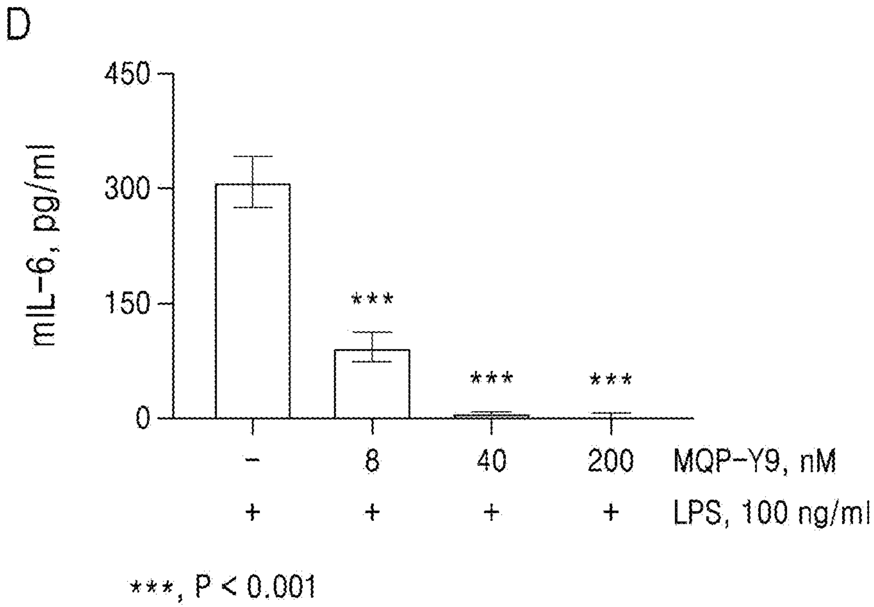

【FIG. 7】
A
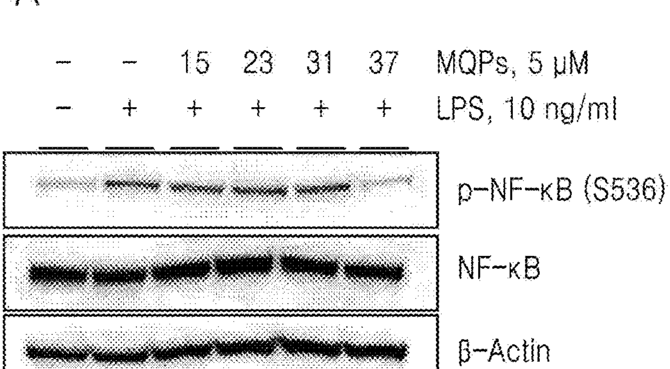
B
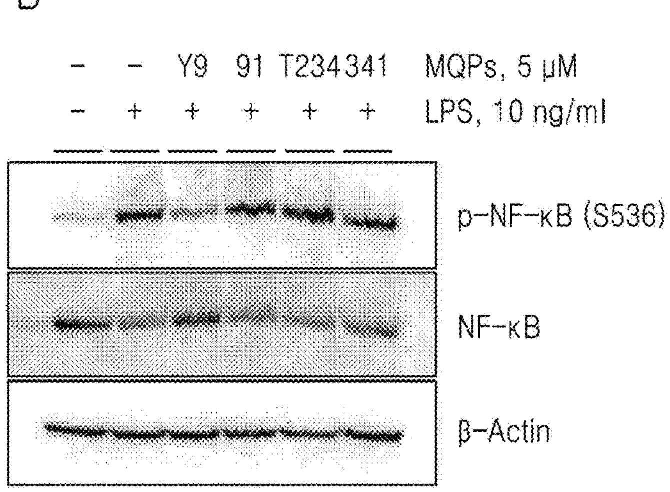

【FIG. 8】
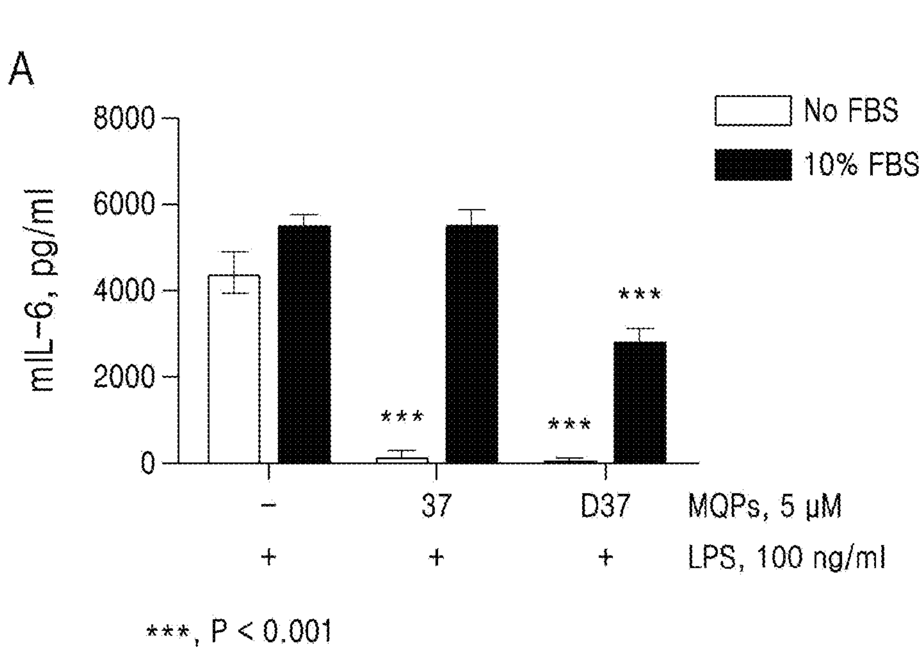
***, P < 0.001
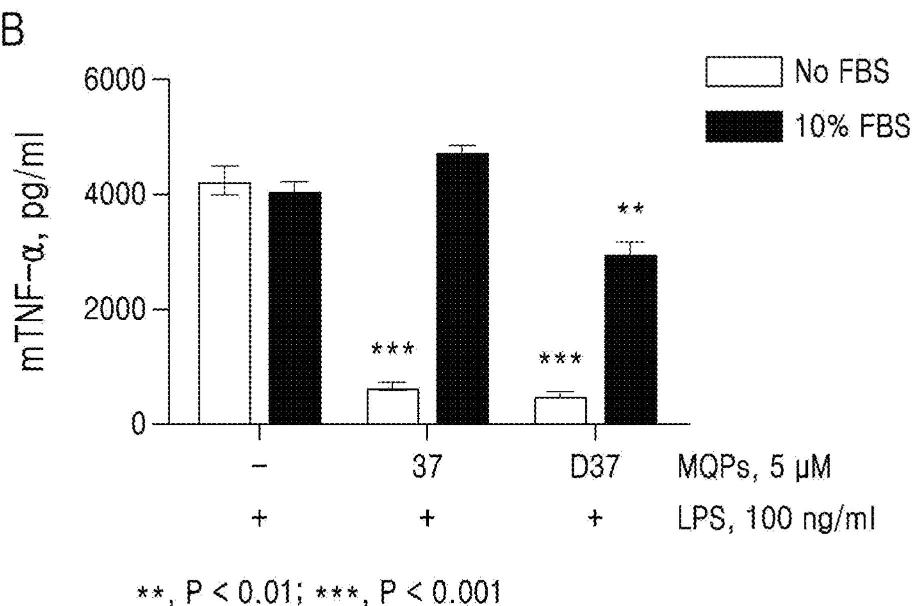
, P < 0.01; *, P < 0.001

【FIG. 9A】
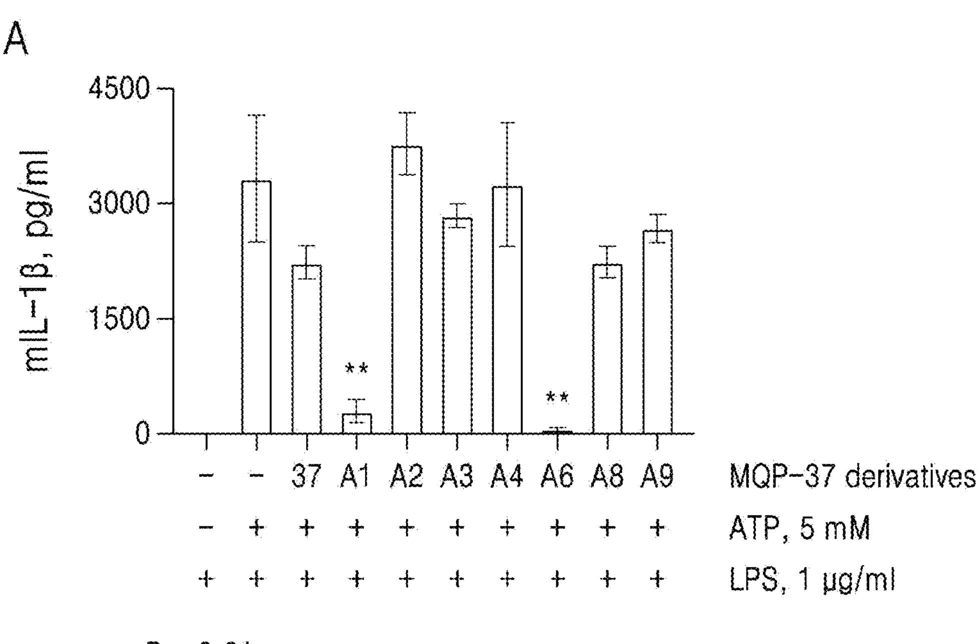
**, P < 0.01
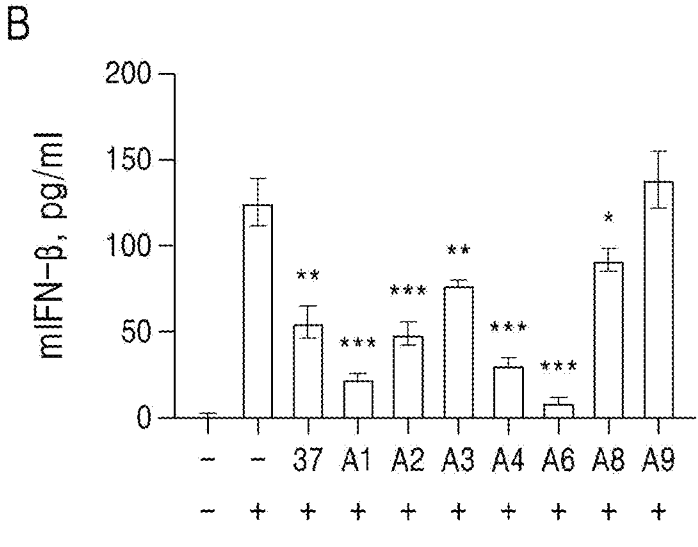
*, P < 0.05; , P < 0.01; *, P < 0.001

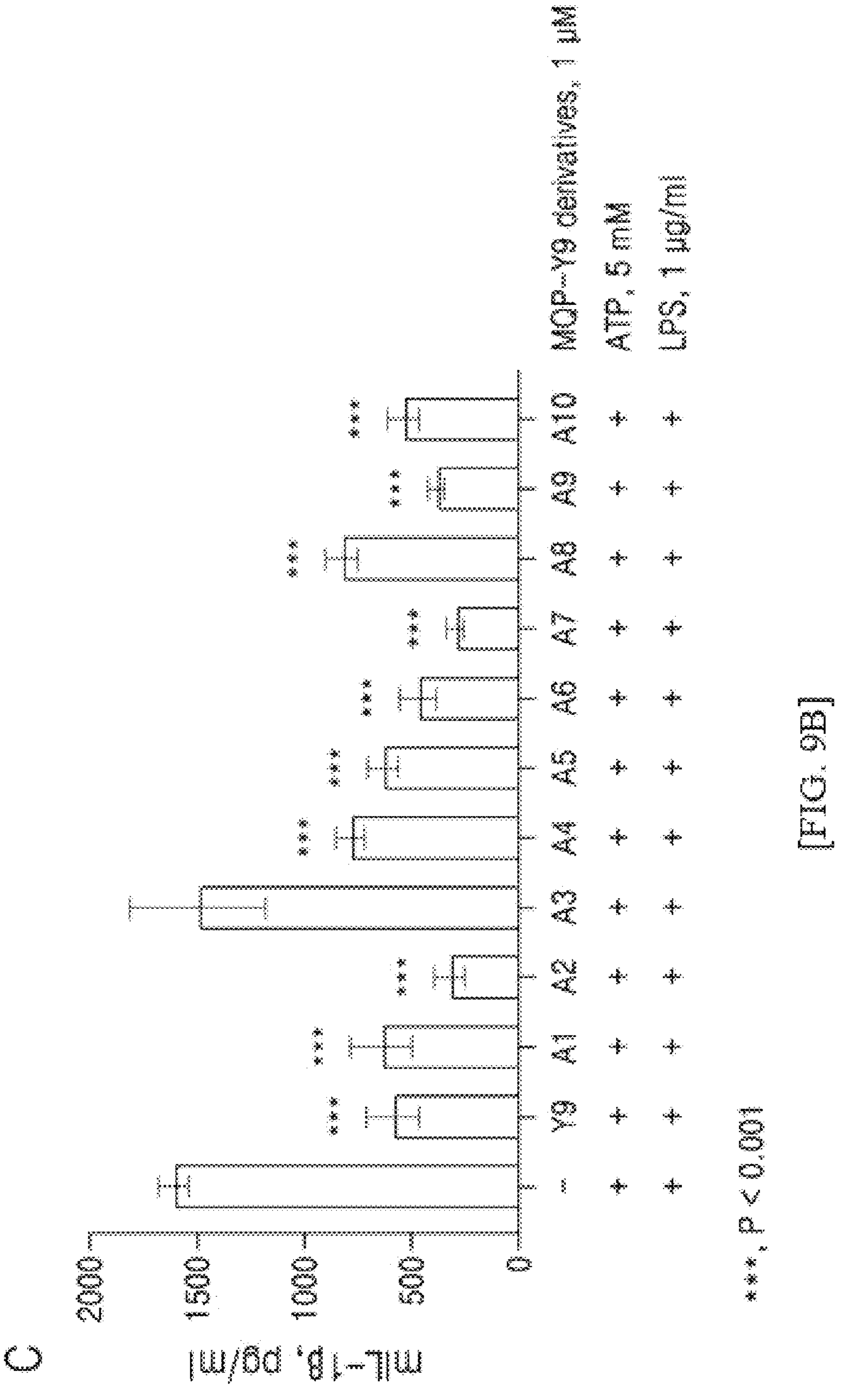
[FIG. 9B]

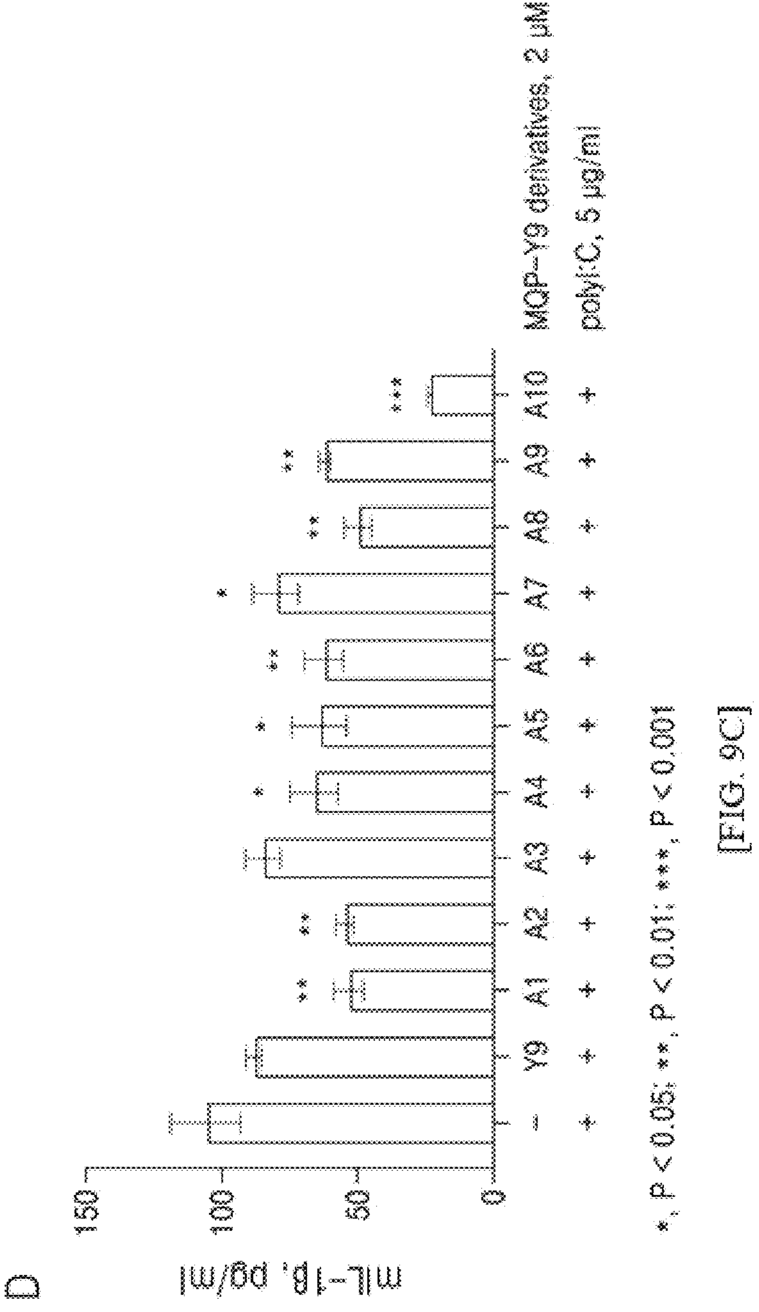
[FIG. 9C]

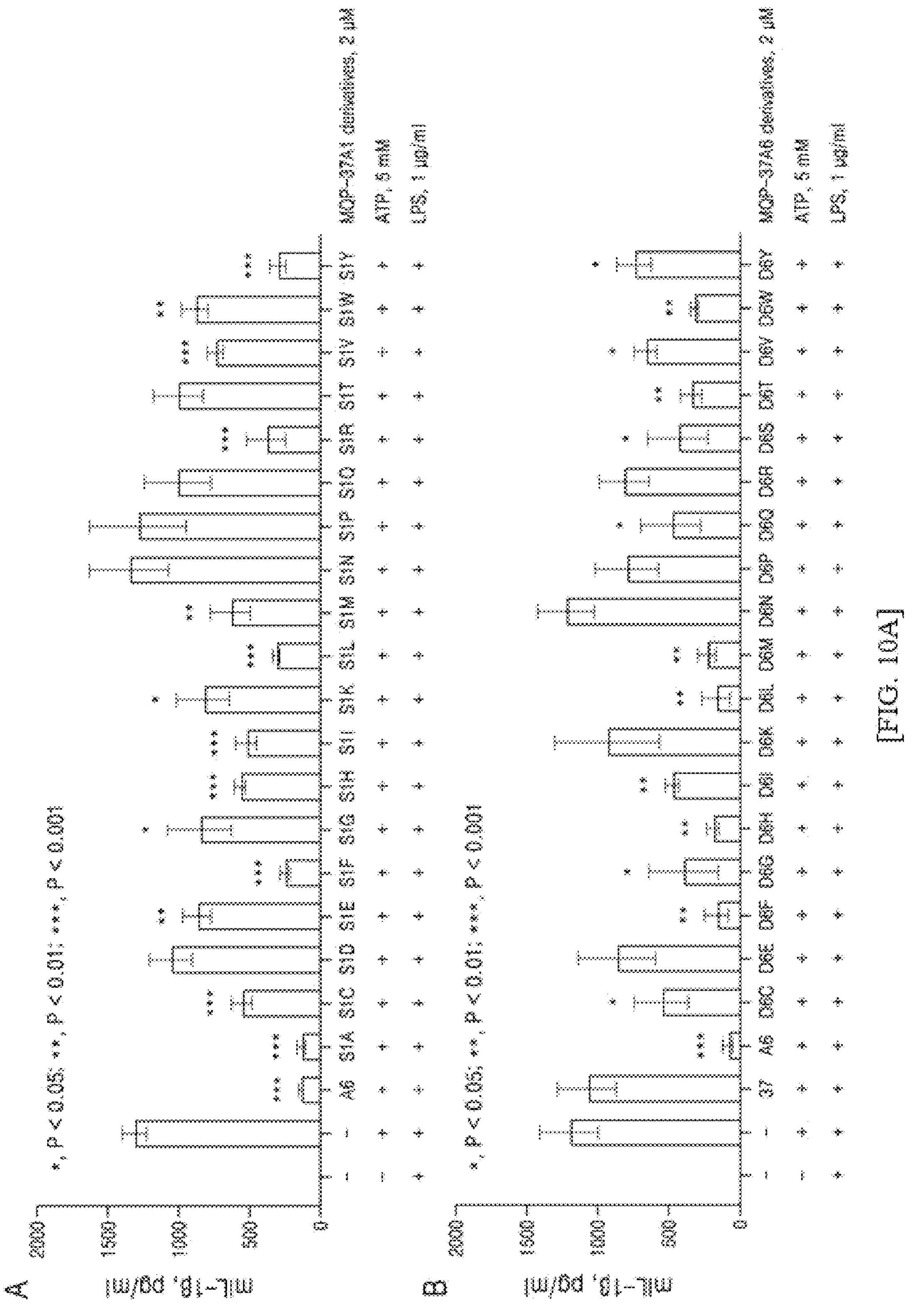
[FIG. 10A]

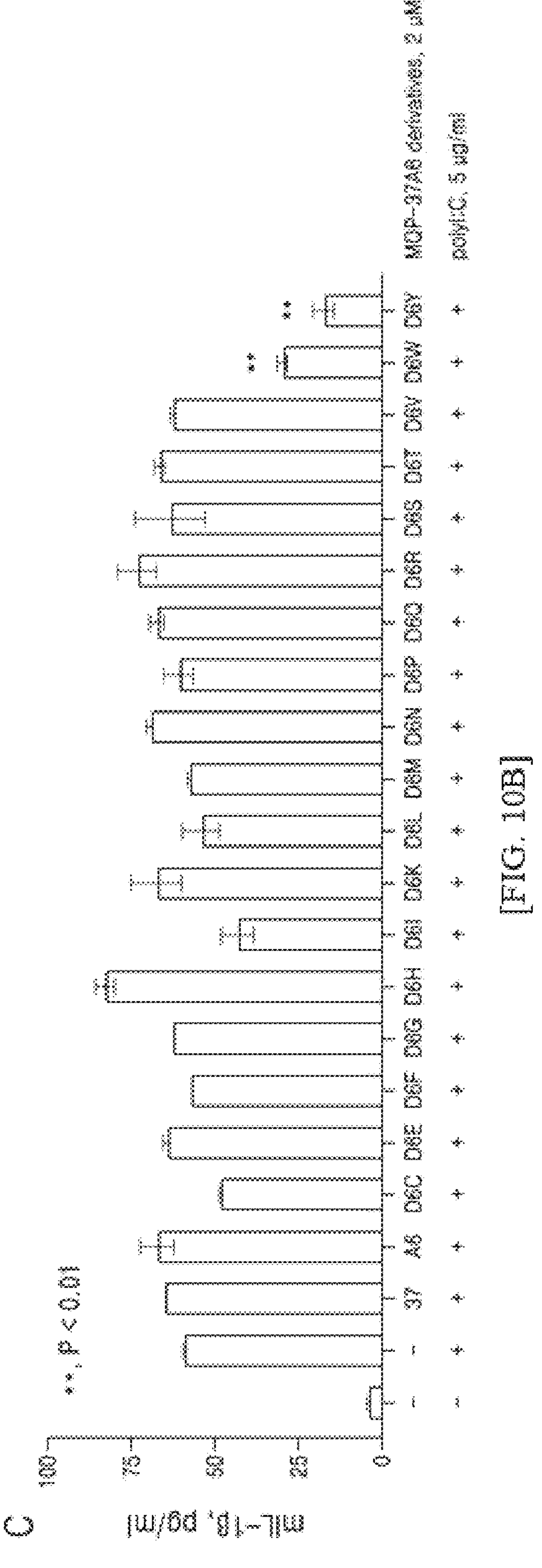
[FIG. 10B]

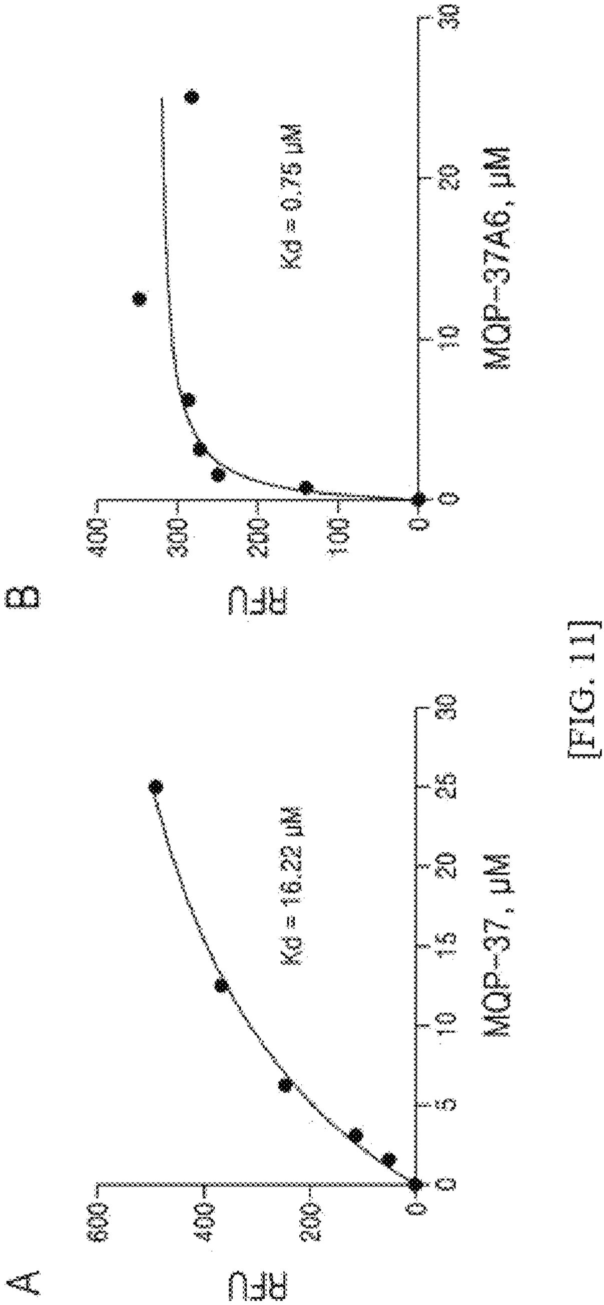
[FIG. 11]

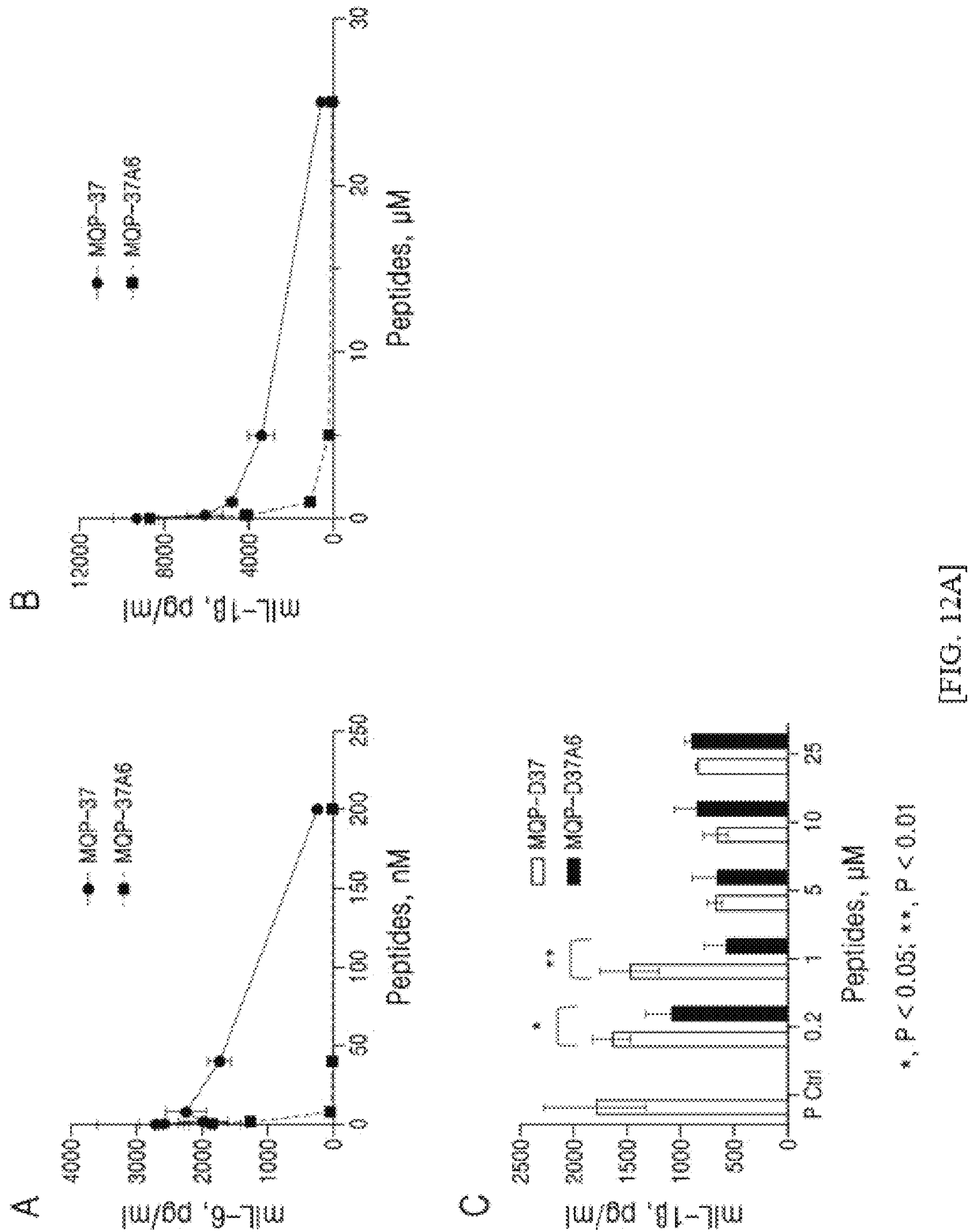
[FIG. 12A]

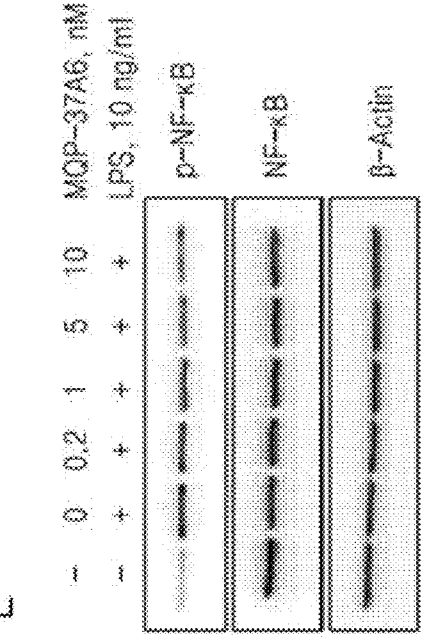
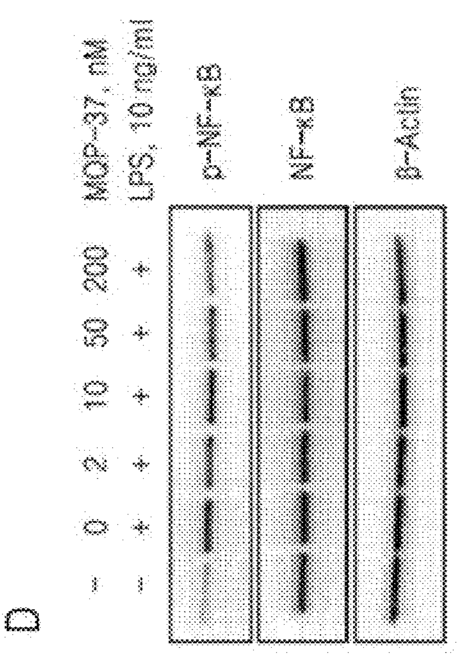
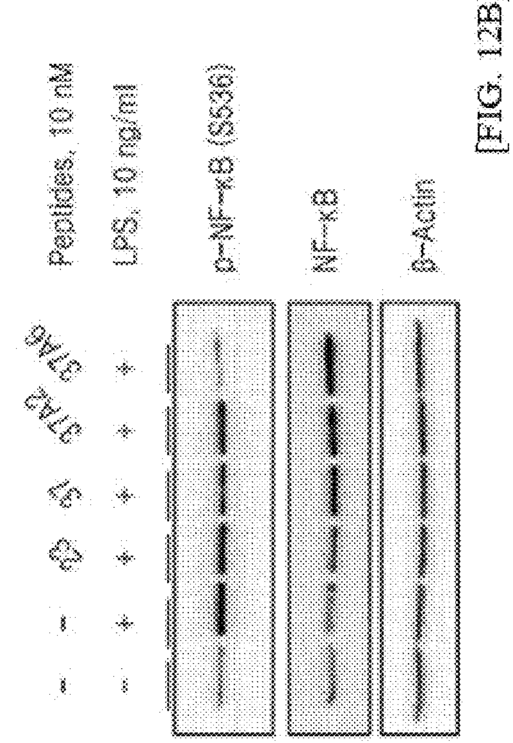
[FIG. 12B]

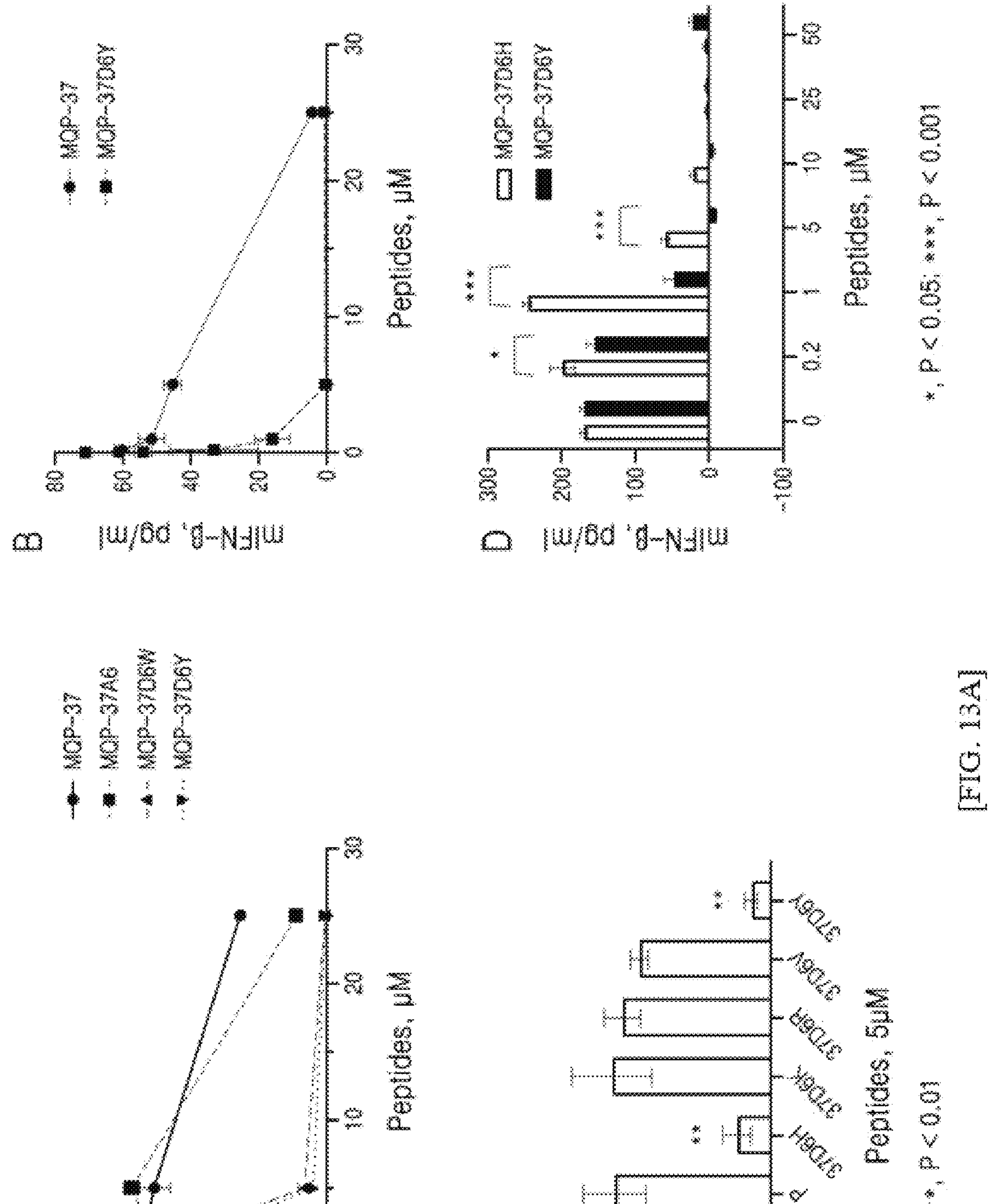
[FIG. 13A]

F
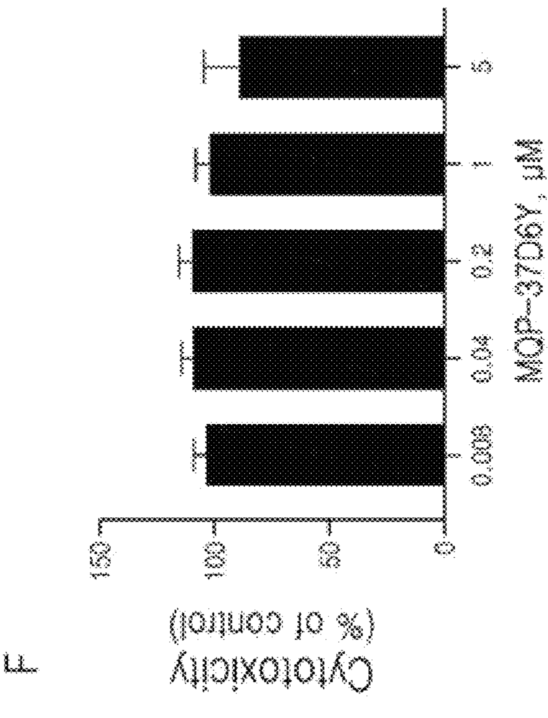
E
Ctrl
pIC (5 μg/ml)
pIC + MOP-37 (5 μM)
pIC + MOP-37D6Y (5 μM)
Original magnification – x100
[FIG. 13B]

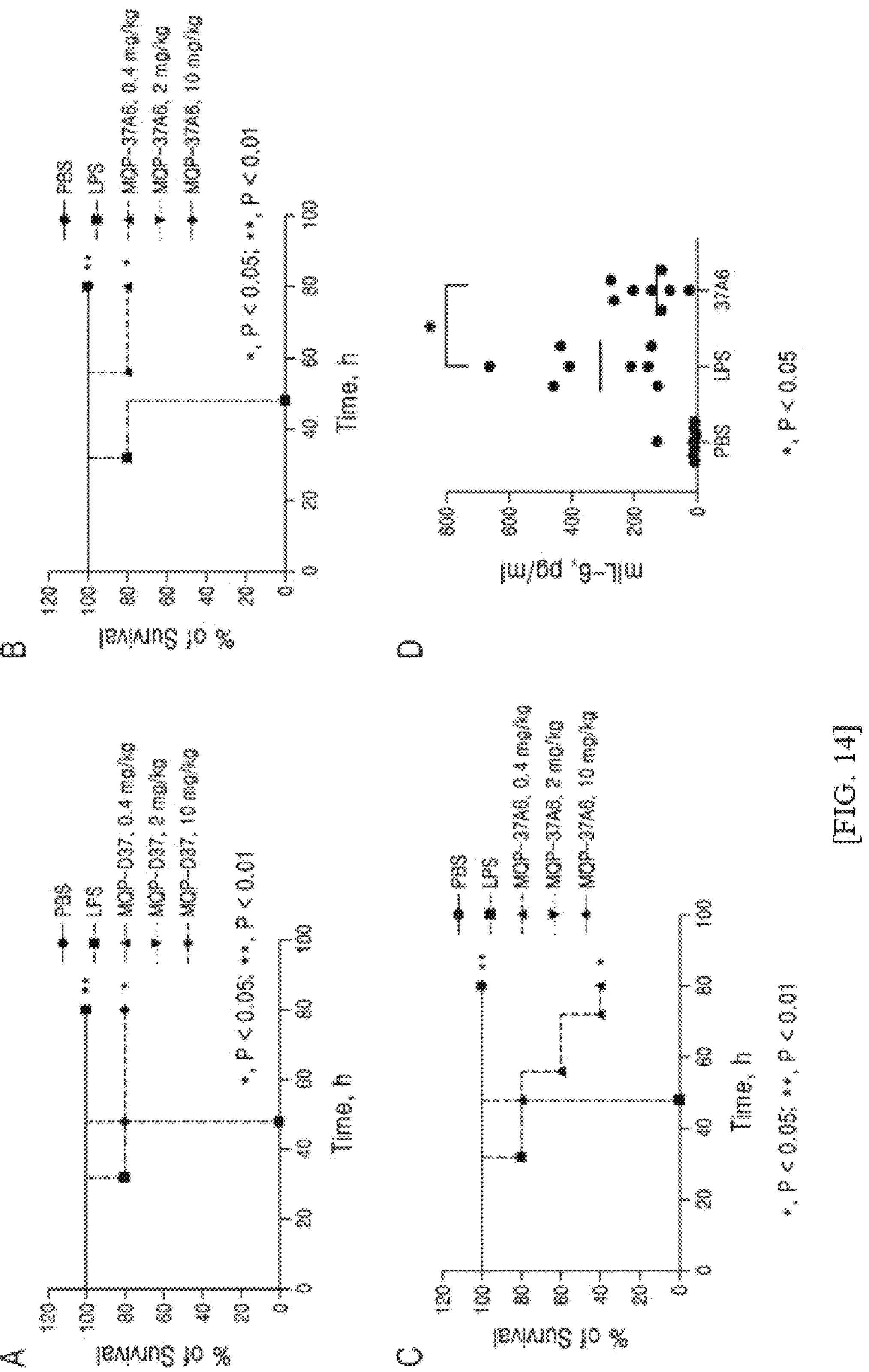
[FIG. 14]

ANTI-INFLAMMATORY PEPTIDE AND USE THEREOF

CROSS-REFERENCE TO RELATED APPLICATIONS

This application is the U.S. National Phase under 35 U.S.C. § 371 of International Application No. PCT/KR2021/006679, filed on May 28, 2021, which in turn claims the benefit of Korean Application No. 10-2020-0064483, filed on May 28, 2020, the disclosures of which are incorporated by reference into the present application.

SEQUENCE LISTING

A SEQUENCE LISTING is submitted in a file named SequenceST25form via EFS Web and is hereby incorporated by reference in its entirety. Said file was created on Nov. 22, 2022, and is 12,389 bytes in size.

TECHNICAL FIELD

The present disclosure relates to an anti-inflammatory peptide including at least one selected from the group consisting of the amino acid sequences of SEQ ID NOS: 1 to 63 and modifications thereof, an anti-inflammatory composition comprising the same, and a pharmaceutical composition for preventing or treating inflammatory diseases.

BACKGROUND

Recently, the proportion of the elderly continues to increase due to the advancement of medical technology and the increase in life expectancy caused by economic development (Chang et al., 1994, Korean J. Gastroentrol., 26:907-918.; Heinzemann and Daser, 2002, Int. Arch. Allergy Immunol. 127:170-180.; Song et al., 1998, Korean J. Intern. Med., 55:158-168.; Sung et al., 2012, J. Ethnopharmacol. 144:94-100.).

In general, the inflammatory response is a defense mechanism of living tissues against external stimulus such as bacterial or viral infection (pathogen-associated molecular pattern (PAMP)) or internal stimulus such as in vivo metabolites following tissue damage (damage-associated molecular pattern (DAMP)), and it is caused by the production of various intracellular inflammatory regulators including cytokines, such as TNF-α (tumor necrosis factor-α), IL-1β (interleukin-1β) and IL-6 (interleukin-6), and nitric oxide (NO). Lipopolysaccharide (LPS), also known as endotoxin, is a representative example of PAMP, and is found in the outer membrane of Gram-negative bacteria. LPS induces gene expression of inflammatory cytokines, iNOS (inducible nitric oxide synthase) and COX-2 (cyclooxygenase-2) by inducing the activation of an intracellular transcription factor NF-κB (nuclear factor-κB) in macrophages or monocytes, and produces inflammatory mediators. Therefore, substances that regulate the inflammatory response (e.g., the expression of iNOS, COX-2 or NF-κB, and the secretion of cytokines and nitric oxide) caused by PAMP or DAMP have recently attracted attention as preventive and therapeutic agents for inflammatory diseases (Dela Cruz and Kang, 2018, Mitochondrion, 41:37-44; Kim et al, 2013b, J. Korean Med. Ophthalmol. Otolaryngol. Dermatol., 26:54-64.).

Examples of substances currently used for anti-inflammatory purposes include flufenamic acid, ibuprofen, benzydamine and indomethacin which are nonsteroids; and prednisolone, dexamethasone, betamethasone and hydrocortisone which are steroids. However, these substances are highly toxic and cause serious side effects such as liver damage, cancer and stroke and thus have limitations when used. Also, these substances may induce severe immunosuppression because they cannot selectively act on substances that cause inflammation. Accordingly, there has been development of anti-inflammatory drugs, which are safe to living bodies and are easier to intake for a long time than conventional drugs, by using natural substances. However, anti-inflammatory substances extracted from natural substances exhibit low effective concentration, and are cultivated in agricultural fields, etc., which results in high production cost.

In order to solve the above problems, a new concept anti-inflammatory drug is being developed as an alternative to conventional chemical anti-inflammatory drugs or anti-inflammatory drugs using natural substances. In particular, a lot of research on the synthesis of peptides having anti-inflammatory activity is being conducted.

However, in general, a synthesized peptide has very good anti-inflammatory activity and does not show cytotoxicity in in vitro experiments, but actually, the anti-inflammatory effect is often insignificant in in vivo experiments.

This is due to several reasons, but this is mainly because physiological and anatomical conditions in vivo are very different from those in vitro. First, in the presence of salt, which is a physiological condition, the activity of a peptide having a low positive charge is significantly inhibited. Second, a peptide has a small molecular weight and size, and, thus, it is almost absorbed by the kidney and excreted out of the body. Third, a peptide is easily cleaved by proteases and peptidases present in all tissues, cells, body fluids and blood in the living body and thus loses its activity.

Under the circumstances, the present inventors have made many efforts to develop a substance exhibiting excellent anti-inflammatory activity while solving the above problems. As a result, the present inventors have developed a peptide suitable for economical mass production by using 5 to 15 typical amino acid residues, and have completed the present disclosure by verifying that the peptide does not show cytotoxicity and exhibits excellent anti-inflammatory activity.

DISCLOSURE OF THE INVENTION

Problems to be Solved by the Invention

The present disclosure relates to an anti-inflammatory peptide including at least one selected from the group consisting of the amino acid sequences of SEQ ID NOS: 1 to 63 and modifications thereof, an anti-inflammatory composition comprising the same, and a pharmaceutical composition for preventing or treating inflammatory diseases.

However, the problems to be solved by this disclosure are not limited to those mentioned above, and other problems not mentioned will be clearly understood by those skilled in the art from the following description.

Means for Solving the Problems

A first aspect of the present disclosure provides an anti-inflammatory peptide including at least one selected from the group consisting of the amino acid sequences of SEQ ID NOS: 1 to 63 and modifications thereof.

A second aspect of the present disclosure provides a polynucleotide that encodes the anti-inflammatory peptide of the present disclosure.

A third aspect of the present disclosure provides an anti-inflammatory composition including the anti-inflammatory peptide of the present disclosure as an active ingredient.

A fourth aspect of the present disclosure provides a pharmaceutical composition for preventing or treating inflammatory diseases, including the anti-inflammatory peptide of the present disclosure as an active ingredient.

Effects of the Invention

An anti-inflammatory peptide according to an embodiment of the present disclosure has no cytotoxicity, and has an effect of inhibiting the activation of mitochondrial antiviral signaling protein (MAVS), immune/inflammatory activation mechanism and the expression or activity of inflammatory cytokines and inflammasomes. Therefore, the peptide can be applied to an anti-inflammatory composition or a composition for treating inflammatory diseases.

BRIEF DESCRIPTION OF THE DRAWINGS

FIG. 1A shows the structures of novel anti-inflammatory peptides developed according to the present disclosure.

FIG. 1B shows the structures of novel anti-inflammatory peptides developed according to the present disclosure.

FIG. 1C shows the structures of novel anti-inflammatory peptides developed according to the present disclosure.

FIG. 1D shows the structures of novel anti-inflammatory peptides developed according to the present disclosure.

FIG. 1E shows the structures of novel anti-inflammatory peptides developed according to the present disclosure.

FIG. 1F shows the structures of novel anti-inflammatory peptides developed according to the present disclosure.

FIG. 2 shows the results of experiments demonstrating the MAVS aggregation inhibitory effect of anti-inflammatory peptides of the present disclosure.

FIG. 3A shows the results of experiments demonstrating the effect of anti-inflammatory peptides of the present disclosure to inhibit the expression of IFN-β induced by polyinosinic:polycytidylic acid (polyIC).

FIG. 3B shows the results of experiments demonstrating the effect of anti-inflammatory peptides of the present disclosure to inhibit the expression of IFN-β induced by polyinosinic:polycytidylic acid (polyIC).

FIG. 4 shows the results of experiments demonstrating the cytotoxicity of anti-inflammatory peptides of the present disclosure.

FIG. 5A shows the results of experiments demonstrating the effect of anti-inflammatory peptides of the present disclosure to inhibit the expression of IL-1β induced by LPS or bacterial outer membrane vesicle (OMV).

FIG. 5B shows the results of experiments demonstrating the effect of anti-inflammatory peptides of the present disclosure to inhibit the expression of IL-1β induced by LPS or bacterial outer membrane vesicle (OMV).

FIG. 5C shows the results of experiments demonstrating the effect of anti-inflammatory peptides of the present disclosure to inhibit the expression of IL-1β induced by LPS or bacterial outer membrane vesicle (OMV).

FIG. 6A shows the results of experiments demonstrating the effect of anti-inflammatory peptides of the present disclosure to inhibit the expression of IL-6 and TNF-α induced by LPS.

FIG. 6B shows the results of experiments demonstrating the effect of anti-inflammatory peptides of the present disclosure to inhibit the expression of IL-6 and TNF-α induced by LPS.

FIG. 7 shows the results of experiments demonstrating the effect of anti-inflammatory peptides of the present disclosure to inhibit the phosphorylation of NF-κB induced by LPS.

FIG. 8 shows the results of experiments demonstrating the protease resistance-increasing effect through modification of anti-inflammatory peptides of the present disclosure.

FIG. 9A shows the results of experiments demonstrating the effect of anti-inflammatory peptides MQP-37 and MQP-Y9 of the present disclosure whose sequence is substituted with alanine to inhibit the production of IL-1b or IFN-b induced by LPS/ATP or polyIC.

FIG. 9B shows the results of experiments demonstrating the effect of anti-inflammatory peptides MQP-37 and MQP-Y9 of the present disclosure whose sequence is substituted with alanine to inhibit the production of IL-1b or IFN-b induced by LPS/ATP or polyIC.

FIG. 9C shows the results of experiments demonstrating the effect of anti-inflammatory peptides MQP-37 and MQP-Y9 of the present disclosure whose sequence is substituted with alanine to inhibit the production of IL-1b or IFN-b induced by LPS/ATP or polyIC.

FIG. 10A shows the results of experiments demonstrating the effect of anti-inflammatory peptide MQP-37 of the present disclosure whose first or sixth sequence is substituted with different 19 amino acids to inhibit the production of IL-1b or IFN-b induced by LPS/ATP or polyIC.

FIG. 10B shows the results of experiments demonstrating the effect of anti-inflammatory peptide MQP-37 of the present disclosure whose first or sixth sequence is substituted with different 19 amino acids to inhibit the production of IL-1b or IFN-b induced by LPS/ATP or polyIC.

FIG. 11 shows the results of experiments comparing the binding force of anti-inflammatory peptides MQP-37 and MQP-37A6 of the present disclosure with respect to MAVS protein.

FIG. 12A shows the results of experiments comparing the physiological activity (the amount of production of IL-6 and IL-1b induced by LPS or LPS/nigericin, phosphorylation of NF-κB induced by LPS) of anti-inflammatory peptides MQP-37 and MQP-37A6 of the present disclosure.

FIG. 12B shows the results of experiments comparing the physiological activity (the amount of production of IL-6 and IL-1b induced by LPS or LPS/nigericin, phosphorylation of NF-κB induced by LPS) of anti-inflammatory peptides MQP-37 and MQP-37A6 of the present disclosure.

FIG. 13A shows the results of experiments comparing the physiological activity (the amount of production of IFN-b induced by polyIC and apoptosis) of anti-inflammatory peptides MQP-37, MQP-37D6Y, MQP-36D6W and QP-37D6H of the present disclosure.

FIG. 13B shows the results of experiments comparing the physiological activity (the amount of production of IFN-b induced by polyIC and apoptosis) of anti-inflammatory peptides MQP-37, MQP-37D6Y, MQP-36D6W and QP-37D6H of the present disclosure.

FIG. 14 shows the results of experiments demonstrating the effect of anti-inflammatory peptides MQP-37 and MQP-37A6 of the present disclosure to treat sepsis in mouse sepsis models induced by LPS.

BEST MODE FOR CARRYING OUT THE INVENTION

A Hereafter, embodiments of the present disclosure will be described in detail with reference to the accompanying drawings so that the present disclosure may be readily implemented by a person with ordinary skill in the art.

However, it is to be noted that the present disclosure is not limited to the embodiments but may be embodied in various other ways. In drawings, parts irrelevant to the description are omitted for the simplicity of explanation, and like reference numerals denote like parts through the whole document.

Throughout this document, the term "connected to" may be used to designate a connection or coupling of one element to another element and includes both an element being "directly connected" another element and an element being "electronically connected" to another element via another element. Further, it is to be understood that the terms "comprises," "includes," "comprising," and/or "including" means that one or more other components, steps, operations, and/or elements are not excluded from the described and recited systems, devices, apparatuses, and methods unless context dictates otherwise; and is not intended to preclude the possibility that one or more other components, steps, operations, parts, or combinations thereof may exist or may be added.

Throughout this document, the term "combination(s)" included in the Makushi-type expression refers to a mixture or combination of at least one selected from the group consisting of components described in the Makushi-type expression, and includes at least one selected from the group consisting of the above components.

Throughout the present specification, the description of "A and/or B" means "A or B, or A and B".

Hereinafter, embodiments and embodiments of the present invention will be described in detail with reference to the accompanying drawings. However, the present disclosure may not be limited to these implementations and embodiments and drawings.

A first aspect of the present disclosure provides an anti-inflammatory peptide including at least one selected from the group consisting of the amino acid sequences of SEQ ID NOS: 1 to 63 and modifications thereof.

The term "peptide" as used throughout the present disclosure refers to a linear molecule formed by amino acid residues connected to each other by peptide bonds (—CO—NH—). The peptide of the present disclosure may be prepared by a chemical synthesis method known in the art, particularly solid-phase synthesis techniques (Merrifield, J. Amer. Chem. Soc. 85:2149-54 (1963); Stewart, et al., Solid Phase Peptide Synthesis, 2nd. ed. and Pierce Chem. Co.: Rockford, 111 (1984)) or liquid-phase synthesis techniques (U.S. Pat. No. 5,516,891), and the amino acid residues constituting the peptide of the present disclosure may be natural or non-natural amino acid residues.

In an embodiment of the present disclosure, the peptide may include at least one selected from the group consisting of the amino acid sequences of SEQ ID NOS: 1 to 63 and modifications thereof, and specifically may include the amino acid sequence of SEQ ID NO: 1.

In an embodiment of the present disclosure, the modifications may maintain their activity without changing the main activity thereof or exhibit improved activity, and may encompass a part of the amino acid sequence varied by natural mutation or artificial mutation or one or more amino acids of the amino acid sequence substituted with other types of amino acids. Specifically, the modifications may include one or more amino acids of the amino acid sequence of SEQ ID NOS: 1 to 63 substituted with at least one selected from the group consisting of gamma amino butanoic acid, glutamine (Gln, Q), glutamic acid (Glu, E), glycine (Gly, G), lysine (Lys, K), leucine (Leu, L), methionine (Met, M), (Val, V), serine (Ser, S), selenomethionine, selenocysteine (Sec, U), cysteine (Cys, C), citrulline, arginine (Arg, R), asparagine (Asn, N), aspartic acid (Asp, D), alanine (Ala, A), ornithine, isoleucine (Ile, I), taurine, threonine (Thr, T), tryptophan (Trp, W), tyrosine (Tyr, Y), phenylalanine (Phe, F), proline (Pro, P), pyrrolysine (Pyr, O), histidine (His, H) and non-natural amino acids. Peptides according to an embodiment of the present disclosure may include the peptide of SEQ ID NOS described above as well as peptides having homology of 80% or more, 85% or more, 90% or more, 91% or more, 92% or more, 93% or more, 94% or more, 95% or more, 96% or more, 97% or more, 98% or more, or 99% or more to the amino acid sequence as long as they have a biological activity identical or corresponding to each of the peptides. It is obvious that any amino acid sequence with deletion, modification, substitution, or addition in part of the sequence can also be included within the scope of the present disclosure as long as the amino acid sequence has a homology to the sequence and has a biological activity substantially identical or corresponding to the peptide of the SEQ ID NOS described above.

The term "homology" as used throughout the present disclosure refers to the degree of matching between given amino acid sequences or polynucleotide sequences and may be expressed as a percentage. In the present disclosure, a homologous sequence having an activity identical or similar to a given amino acid sequence or polynucleotide sequence is represented by "% homology". For example, homology may be confirmed using standard software, specifically BLAST 2.0, for calculating parameters such as score, identity and similarity or by comparing sequences by hybridization experiments under defined stringent conditions. Defined appropriate hybridization conditions may be within the scope of the art and may be determined by a method well known to a person with ordinary skill in the art [e.g., J. Sambrook et al., Molecular Cloning, A Laboratory Manual, 2nd Edition, Cold Spring Harbor Laboratory press, Cold Spring Harbor, New York, 1989; F. M. Ausubel et al., Current Protocols in Molecular Biology, John Wiley & Sons, Inc., New York]. The term "stringent conditions" as used throughout the present disclosure refers to conditions which enables specific hybridization between polynucleotides. For example, such conditions are specifically described in literatures (e.g., J. Sambrook et al., supra).

The term "anti-inflammation" as used throughout the present disclosure refers to an action of inhibiting or reducing inflammation, and the term "inflammation" is a defense response occurring in the body when living tissue is damaged and causes an inflammatory disease. Therefore, the anti-inflammatory peptide of the present disclosure exhibits an activity of inhibiting or reducing inflammation and thus can be used for prevention, treatment or amelioration (relief of symptoms) of an inflammatory disease.

In an embodiment of the present disclosure, the peptide may further include a cell-penetrating peptide, but is not limited thereto.

The term "cell-penetrating peptide" as used throughout the present disclosure is a peptide having the ability or property to penetrate through the cell membrane and penetrate into the cell, and may indicate cell penetrability and/or skin penetrability.

In an embodiment of the present disclosure, the cell-penetrating peptide may further include a part or all of a sequence derived from a conventionally known cell-penetrating peptide or a skin-penetrating peptide, and may include a member selected from the group consisting of, for example, dNP2, penetratin, Tat, transpotan, MAP, KALA, P1, MPG, Pep-1, Arg (7, 8, 9, 10, 11), hCT, pVEC, SPEH, YARA, WLR, VP22, MTS, FHV coat, and combinations thereof. Specifically, the cell-penetrating peptide may be an Arg(8) peptide (R8 peptide), but may not be limited thereto.

In an embodiment of the present disclosure, the cell-penetrating peptide may be included in the anti-inflammatory peptide twice or more. Specifically, the cell-penetrating peptide may be included twice, three times, five times, seven times or ten times, but is not limited thereto.

In an embodiment of the present disclosure, the cell-penetrating peptide may be linked to the N- or C-terminus of the anti-inflammatory peptide. Specifically, the cell-penetrating peptide may be linked to the N-terminus, but is not limited thereto as long as it can improve cell penetrability or skin penetrability without inhibiting the pharmacological activity of the peptide.

In an embodiment of the present disclosure, the cell-penetrating peptide may be linked to the anti-inflammatory peptide through a linker or may be directly linked to the anti-inflammatory peptide. Further, the linker may be cleaved or degraded by various biological and chemical actions such as enzyme actions in cells or skin. As the linker is cleaved or degraded, the cell-penetrating peptide and the anti-inflammatory peptide may be separated from each other in targeted cells or skin.

In an embodiment of the present disclosure, amino acids constituting the anti-inflammatory peptide may be L-type or D-type. Specifically, the amino acids constituting the anti-inflammatory peptide may be D-type, but are not limited thereto as long as they do not affect the activity of the peptide.

In an embodiment of the present disclosure, the N- or C-terminus of the anti-inflammatory peptide may be linked to a protective group selected from the group consisting of an acetyl group, a fluorenyl methoxy carbonyl group, a formyl group, a palmitoyl group, a myristyl group, a stearyl group and polyethylene glycol (PEG), and the protective group is not limited thereto as long as it does not affect the activity of the peptide.

In an embodiment of the present disclosure, the peptide or amino acids constituting the same may be acetylated or amination as well as the above protective group bond, and the modification greatly improves the stability of the peptide. The stability refers to in vivo stability and storage stability (for example, storage stability at room temperature) as well. The above-described protective group may serve to protect the peptide of the present disclosure from the attack of protease in vivo.

In an embodiment of the present disclosure, the peptide may inhibit the aggregation of mitochondrial antiviral-signaling (MAVS) proteins and/or the function thereof.

As used throughout the present disclosure, the term "MAVS (mitochondrial antiviral-signaling) protein" is a signaling protein essential for anti-viral innate immunity, and is known to be present in the outer membrane of mitochondria, peroxisome and endoplasmic reticulum (ER). The MAVS protein is activated by forming an aggregate by a cytoplasmic protein group that detects the presence of a virus upon viral infection, and the activated MAVS protein induces an immune response in a manner that induces the secretion of interferons and cytokines. However, if the MAVS protein is continuously activated and the production of interferons and cytokines is excessively increased, it may attack cells in the body and cause various pathological abnormalities and immune diseases. Therefore, the activation of the MAVS protein needs to be regulated properly.

In an embodiment of the present disclosure, the anti-inflammatory peptide inhibits MAVS aggregation or activation and thus can inhibit the inflammatory/immune activation response mechanism and inflammatory/immune response induced by MAVS activation and can also treat, prevent or ameliorate symptoms or diseases that can be developed by MAVS aggregation.

In an example of the present disclosure, it was confirmed that the anti-inflammatory peptide of the present disclosure effectively inhibits MAVS aggregation induced by the pathogen-associated molecular pattern (PAMP) derived from bacteria and viruses. Thus, it can be seen that the anti-inflammatory peptide of the present disclosure can effectively suppress inflammatory responses by inhibiting MAVS activity.

In an embodiment of the present disclosure, the peptide may inhibit the expression, generation, activity, etc. of inflammatory cytokine or inflammasome or inhibit the proliferation of inflammatory cells. Specifically, the inflammatory cytokine may be at least one selected from the group consisting of IFN-β, IL-1β, IL-6 and TNF-α, but is not limited thereto as long as it is a substance known to cause an inflammatory response in the art.

As used throughout the present disclosure, the term "inflammasome" refers to a substance that induces the maturation of inflammatory cytokines such as IL-1 related to innate immune defenses such as cellular infection or stress, and is a caspase-1-activating protein complex composed of 1) a sensor protein, NLRP3 (NOD-like receptor family, pyrin domain-containing 3), 2) an adapter protein, ASC (adaptor protein apoptosis-associated spec-like protein containing a caspase-recruitment domain), and 3) an effector protein, inactive caspase-1. The components of the inflammasome are assembled when infection of microorganisms such as bacteria or viruses or tissue damage occurs, and the inflammasome activated by assembly in the cytoplasm converts the inactive caspase-1 into the active caspase-1. The active caspase-1 is known to cleave the precursor form of IL-1β or IL-18 to produce the activated IL-1β or IL-18, and secrete it out of cells to perform the innate immune defense of the host.

In an example of the present disclosure, it was confirmed that the anti-inflammatory peptide of the present disclosure suppresses the expression levels of various inflammatory cytokines and inflammasomes. Thus, it can be seen that the anti-inflammatory peptide of the present disclosure can effectively inhibit inflammatory responses.

In an embodiment of the present disclosure, the peptide may inhibit the mechanism of an inflammatory/immune activation response, and the mechanism may be a caspase-1, an interferon regulatory factor 3 (IRF3) or a nuclear factor kappa-light-chain-enhancer of activated B cells (NF-κB), but is not limited thereto as long as it is a mechanism known to cause an inflammatory/immune response in the art.

In an embodiment of the present disclosure, it was confirmed that the anti-inflammatory peptide of the present disclosure inhibits the activity of NF-κB signaling mechanism by inhibiting the phosphorylation of NF-κB. Thus, it can be seen that the anti-inflammatory peptide of the present disclosure can effectively inhibit inflammatory responses.

In an embodiment of the present disclosure, the peptide may inhibit inflammation induced by bacteria or viruses. Specifically, the peptide may inhibit inflammation induced by the PAMP derived from bacteria or viruses. Also, the peptide may inhibit inflammation caused by the damage-associated molecular pattern (DAMP) secreted out of cells through cell damage caused by bacterial or viral infection.

As used throughout the present disclosure, the term "pathogen-associated molecular pattern (PAMP)" refers to a molecule that originates from a pathogen and causes an immune response. The immune system's pattern recognition receptors respond to specific types of molecules and induce phagocytosis to clear the infectious agent or form antibodies. The common molecular type of infectious agents to which pattern recognition receptors respond can be said to be pathogen-associated molecular patterns. The PAMP may be endotoxin, exotoxin, LPS (lipopolysaccharide), LTA (lipoteichoic acid), MDP (muramyl dipeptide), nigericin, dsRNA (polyIC, etc.), dsDNA (polydAdT, etc.), OMV (outer membrane vesicle) and flagellin, but is not limited thereto as long as it is a substance known to be derived from a pathogen and cause inflammatory/immune responses in the art.

As used throughout the present disclosure, the term "damage-associated molecular pattern (DAMP)" refers to an intracellular metabolite or protein that is secreted out of cells by cell damage and causes an immune response in surrounding cells. The DAPM may be ATP, histone protein, HMGB1 (high mobility group box 1), mtDNA (mitochondrial DNA), uric acid, etc., but is not limited thereto as long as it is a substance known to originate inside cells and cause inflammatory/immune responses in the art.

In an embodiment of the present disclosure, the peptide can inhibit inflammatory responses or treat or alleviate symptoms of diseases caused by inflammatory responses. Specifically, the peptide may be included in various compositions such as anti-inflammatory pharmaceutical composition, food composition, cosmetic composition, health functional food composition, feed composition and the like.

A second aspect of the present disclosure provides a polynucleotide that encodes the anti-inflammatory peptide of the present disclosure. The features described above in respect of the first aspect of the present disclosure may equally apply to the polynucleotide according to the second aspect of the present disclosure.

As used throughout the present disclosure, the term "polynucleotide" refers to a high molecular material to which nucleotides are bound, and to a DNA that encodes genetic information.

In an embodiment of the present disclosure, the polynucleotide may include a base sequence encoding at least one of the amino acid sequence of SEQ ID NOS: 1 to 63.

In an embodiment of the present disclosure, the base sequence encoding the anti-inflammatory peptide includes a base sequence encoding the amino acid described by each sequence number as well as any base sequence having 80% or more, specifically 90% or more, more specifically 95% or more, much more specifically 98% or more and most specifically 99% or more homology to the sequence without limitation as long as it encodes a protein exhibiting efficacy substantially identical or corresponding to that of each peptide. Further, it is apparent that as long as an amino acid sequence has homology to the above sequence and has a biological activity substantially identical or corresponding to that of the peptide of the described sequence number, an amino acid sequence having deletion, modification, substitution or addition in some sequence is also included in the scope of the present disclosure. Furthermore, the polynucleotide encoding the peptides may undergo various modifications in a coding region without changing the amino acid sequence of the peptide expressed from the coding region due to codon degeneracy, in consideration of codons preferred in an organism in which the peptide is to be expressed. Therefore, the polynucleotide may include any polynucleotide sequence without limitation as long as it encodes each protein. Moreover, probes that can be prepared from known sequences, for example any sequence encoding a protein having the activity of the peptide through hybridization with sequences complementary to all or part of the polynucleotide sequence under stringent conditions may be included without limitation.

As used throughout the present disclosure, the term "stringent conditions" refers to conditions that enable specific hybridization between polynucleotides. These conditions are specifically described in documents (see, for example, Sambrook et al., Supra, 9.50-9.51, 11.7-11.8). For example, the stringent conditions may include conditions where genes with high homology, 40% or more homology, specifically 90% or more homology, more specifically 95% or more homology, much more specifically 97% or more homology and particularly 99% or more homology, are hybridized, and genes with homology lower than that are not hybridized, or typical washing conditions for southern hybridization, i.e., washing once, specifically twice or three times at salt concentration and temperature corresponding to 60° C., 1×SSC and 0.1% SDS, specifically 60° C., 0.1×SSC and 0.1% SDS, and more specifically 68° C., 0.1×SSC and 0.1% SDS. Hybridization requires that two polynucleotides have complementary sequences although mismatch between bases is possible depending on the stringency of hybridization. The term "complementary" is used to describe the relationship between nucleotide bases that can hybridize with each other. For example, with respect to DNA, adenosine is complementary to thymine and cytosine is complementary to guanine. Thus, the present disclosure may also include isolated polynucleotide fragments that are complementary to the whole sequence as well as substantially similar polynucleotide sequences.

Specifically, polynucleotides having homology may be detected using hybridization conditions including hybridization processes at a Tm value of 55° C. and using the above-described conditions. Further, the Tm value may be 60° C., 63° C. or 65° C., but is not limited thereto, and may be appropriately controlled by a person with ordinary skill in the art according to the purpose of use. The appropriate stringency for hybridizing polynucleotides depends on the length and degree of complementarity of the polynucleotides, and the variables are well known in the art (see Sambrook et al., Supra, 9.50-9.51, 11.7-11.8).

Another embodiment of the second aspect of the present disclosure provides an expression vector including the polynucleotide.

As used throughout the present disclosure, the term "expression vector" refers to a recombinant vector that is introduced into a suitable host cell and can express a target protein, and to a gene construct including essential regulatory elements operably linked to express a gene insert.

As used throughout the present disclosure, the term "operably linked" means a functional linkage between a nucleic acid expression regulatory sequence and a nucleic acid sequence encoding a target protein in such a manner as to allow general functions. The operable linkage to a recombinant vector may be prepared using a genetic recombinant technique well known in the art, and site-specific DNA cleavage and ligation may be easily performed using enzymes commonly known in the art.

The suitable expression vector of the present disclosure may include a signal sequence for membrane targeting or secretion in addition to expression control elements such as a promoter, an initiation codon, a termination codon, a polyadenylation signal and an enhancer. The initiation and termination codons are generally considered to be a part of the nucleotide sequence encoding an immunogenic target protein, must have activity in a subject when the gene construct is administered, and must be in frame with a coding sequence. A general promoter may be constitutive or inducible. In prokaryotic cells, the promoter includes lac, tac, T3 and T7 promoters, and in eukaryotic cells, the promoter includes a monkey virus 40 (SV40) promoter, a mouse mammary tumor virus (MMTV) promoter, a human immunodeficiency virus (HIV) promoter such as a long terminal repeat (LTR) promoter of HIV, a Moloney virus promoter, a cytomegalovirus (CMV) promoter, an Epstein Barr virus (EBV) promoter, a Rous sarcoma virus (RSV) promoter, a β-actin promoter, and promoters derived from human hemoglobin, human muscle creatine and human metallothionein, but the present disclosure is not limited thereto.

Further, the expression vector may include a selective marker for selecting host cells containing the vector. The selective marker functions to select cells transformed by the vector, and may include markers that impart selectable phenotypes such as drug resistance, auxotrophy, resistance to a cytotoxic agent, or expression of a surface protein. Since only the cells expressing the selective marker survive in an environment treated with a selective agent, it is possible to select the transformed cells. Furthermore, when the vector is a replicable expression vector, the vector may include a replication origin which is a specific nucleic acid sequence in which replication is initiated.

As a recombinant expression vector for inserting a foreign gene, various types of vectors including plasmids, viruses, cosmids and the like may be used. The type of recombinant vector is not particularly limited as long as it can function to express a desired gene and produce a desired protein in various types of eukaryotic and prokaryotic host cells. However, specifically, a vector capable of mass-producing a promoter having strong activity and a foreign protein having a similar form to a natural state while retaining strong expression may be used.

To express the anti-inflammatory peptide according to the present disclosure, various combinations of hosts and vectors may be used. Expression vectors suitable for eukaryotic hosts may include, but are not limited to, expression control sequences derived from SV40, bovine papillomavirus, adenovirus, adeno-associated virus, cytomegalovirus and retrovirus. Expression vectors that may be used in bacterial hosts may include, but are not limited to, bacterial plasmids obtained from *Escherichia coli*, including pET, pRSET, pBluescript, pGEX2T, pUC, col E1, pCR1, pBR322, pMB9, or derivatives thereof, plasmids with a broad host range such as RP4, phage DNA exemplified by phage lambda derivatives such as λgt10, λgt11 or NM989, and other DNA phages such as M13 and filamentous single-stranded DNA phage. A 2° C. plasmid or a derivative thereof may be used for yeast cells, and pVL941 or the like may be used for insect cells.

Another embodiment of the second aspect of the present disclosure provides a non-human transformant including the expression vector.

As used throughout the present disclosure, the term "transformant" may refer to a host cell into which the expression vector can be introduced. Specifically, the transformant of the present disclosure may be a transformant from a source other than a human, but is not limited thereto.

The host cell suitable for introduction of the vector may be a prokaryotic cell such as *Escherichia coli, Bacillus subtilis, Streptomyces* sp., *Pseudomonas* sp., *Proteus mirabilis* or *Staphylococcus* sp. Further, the host cell may be fungus such as *Aspergillus* sp., yeast such as *Pichia pastoris, Saccharomyces cerevisiae, Schizosaccharomyces* sp., or *Neurospora crassa*, other lower eukaryotic cells, or higher eukaryotic cell such as plant or insect cells. Furthermore, the host cell may be a mammalian cell. Specifically, monkey kidney cells 7 (COS7), NSO cells, SP2/0, Chinese hamster ovary (CHO) cells, W138, baby hamster kidney (BHK) cells, MDCK, myeloma cell lines, HuT 78 cells or HEK293 cells may be used, but the present disclosure is not limited thereto.

A transformation method of the present disclosure includes any method of introducing a nucleic acid into an organism, cell, tissue or organ, and may be performed by selecting a suitable standard technique according to a host cell known in the art. Specifically, the method includes electroporation, protoplasma fusion, calcium phosphate ($CaPO_4$) precipitation, calcium chloride ($CaCl_2$)) precipitation, agitation using silicon carbide fibers, *agrobacterium*-mediated transformation, PEG, dextran sulfate, lipofectamine, and dry/inhibition-mediated transformation methods, but is not limited thereto.

Another embodiment of the second aspect of the present disclosure provides a method of producing an anti-inflammatory peptide including a process of culturing the transformant.

The method of producing an anti-inflammatory peptide includes culturing the transformant according to the present disclosure. Specifically, the method of producing an anti-inflammatory peptide may include: a process of constructing an expression vector by inserting a polynucleotide sequence encoding the anti-inflammatory peptide into a vector; a process of producing a transformant by introducing the expression vector into a host cell; a process of culturing the transformant; and a process of isolating and purifying the anti-inflammatory peptide from the cultured transformant.

More specifically, the peptide may be mass-produced by culturing the transformant in a nutrition medium, and medium and culture conditions may be appropriately selected and used depending on a host cell. Conditions such as the temperature, the pH of the medium, the culture time and the like may be appropriately adjusted to be suitable for cell growth and the mass production of proteins during culture.

The recombinant peptide or protein produced as described above may be collected from the medium or cell lysate. A membrane-binding type may be dissociated from a membrane with a suitable surfactant solution (for example, Triton-X 100) or by enzymatic cleavage. Cells used in the expression of anti-OSCAR antibodies or their fragments may be disrupted by various physical or chemical methods such as freeze-thaw purification, sonication, mechanical disruption or a cytolysis agent, and may be isolated and purified using conventional biochemical separation techniques (Sambrook et al., Molecular Cloning: A Laboratory Manual, 2nd Ed., Cold Spring Harbor Laboratory Press (1989); Deuscher, M., Guide to Protein Purification Methods Enzymology, Vol. 182. Academic Press. Inc., San Diego, CA (1990)). Electrophoresis, centrifugation, gel filtration, precipitation, dialysis, chromatography (ion exchange chromatography, affinity chromatography, immunosorbent chromatography, size-exclusion chromatography and the like), isoelectric focusing, various variations thereof, and various combinations thereof may be used, but the present disclosure is not limited thereto.

A third aspect of the present disclosure provides an anti-inflammatory composition including the anti-inflammatory peptide of the present disclosure as an active ingredient.

The features described above in respect of the first aspect and the second aspect of the present disclosure may equally apply to the composition according to the third aspect of the present disclosure.

In an embodiment of the present disclosure, the anti-inflammatory composition may be used as pharmaceutical, quasi-drug, cosmetic, food and feed compositions.

In an embodiment of the present disclosure, the composition may further include a pharmaceutically acceptable salt. Specifically, the pharmaceutically acceptable salt may be, for example, hydrochloride, sulfate, phosphate, acetate, citrate, tartrate, succinate, lactate, maleate, fumarate, oxalate, methanesulfonate or para-toluenesulfonate.

In an embodiment of the present disclosure, the pharmaceutical composition may include a pharmaceutically acceptable carrier in addition to the active ingredient, and may be prepared in an oral dosage form or a parenteral dosage form depending on the route of administration by a conventional method known in the art. Herein, the term "pharmaceutically acceptable" means that a substance to be applied (prescribed) does not have toxicity beyond adaptable without inhibiting the activity of the active ingredient.

In an embodiment of the present disclosure, the pharmaceutical composition may be formulated and used in an oral dosage form, such as powder, granule, tablet, capsule, suspension, emulsion, syrup and aerosol, external preparation, suppository or sterile injection solution by conventional methods, respectively, but is not limited thereto.

In an embodiment of the present disclosure, the pharmaceutical composition may be formulated with fillers, extenders, binders, wetting agents, disintegrating agents, diluents including surfactants or excipients which are generally used in the art, but is not limited thereto.

In an embodiment of the present disclosure, when the pharmaceutical composition is prepared in the oral dosage form, it may be prepared in combination with a suitable carrier in the form of powder, granule, tablet, pill, troch, capsule, liquid, gel, syrup, suspension and wafer by a method known in the art. Examples of suitable pharmaceutically acceptable carriers include sugars such as lactose, glucose, sucrose, dextrose, sorbitol, mannitol, xylitol etc., starches such as corn starch, potato starch, wheat starch, etc., celluloses such as cellulose, methyl cellulose, ethyl cellulose, sodium carboxymethyl cellulose, hydroxypropyl methyl cellulose, etc., polyvinylpyrrolidone, water, methyl hydroxy benzoate, propyl hydroxy benzoate, magnesium stearate, mineral oil, malt, gelatin, talc, polyol, vegetable oil and the like. The pharmaceutical composition may be formulated to include fillers, extenders, binders, wetting agents, disintegrating agents, diluents including surfactants and/or excipients if necessary.

In an embodiment of the present disclosure, when the pharmaceutical composition is formulated in a parenteral dosage form, it may be prepared in combination with a suitable carrier in the form of injection, transdermal preparation, nasal inhaler or suppository by a method well known in the art. Examples of carriers suitable for injection may include sterile water, ethanol, polyols such as glycerol or propylene glycol) or combinations thereof. Preferably, the carriers may be an isotonic solution such as a Ringer's solution, triethanol amine-containing PBS (phosphate buffered saline) or injectable sterile water and 5% dextrose. When the pharmaceutical composition is formulated in the parenteral dosage form, it may be formulated in the form of ointment, cream, lotion, gel, external solution, paste, liniment, aerosol and the like. The nasal inhaler may be formulated in the form of aerosol spray using a suitable propellant such as dichlorofluoromethane, trichlorofluoromethane, dichlorotetrafluoroethane, carbon dioxide, etc. When the pharmaceutical composition is formulated in the form of a suppository, Witepsol, tween 61, polyethylene glycols, cacao butter, laurin fat, polyoxyethylene sorbitan fatty acid esters, polyoxyethylene stearates, sorbitan fatty acid esters, etc. may be used as a base agent.

In an embodiment of the present disclosure, the pharmaceutical composition may be administered in a pharmaceutically effective amount. The term "pharmaceutically effective amount" refers to an amount sufficient to prevent or treat a disease at a reasonable benefit/risk ratio applicable to a medical treatment or prevention. An effective dosage level may be determined depending on factors including severity of the disease, drug activity, a patient's age, body weight, health conditions, gender, sensitivity to the drug, administration time, administration route and excretion rate of the composition of the present disclosure, duration of treatment, drugs blended with or co-administered with the composition of the present disclosure, and other factors known in the medical field. The pharmaceutical composition of the present disclosure may be administered individually or in combination with a known ingredient for treating intestinal diseases. It is important to administer the composition in the minimum amount that may exhibit the maximum effect without causing side-effects, in view of all of the above-described factors.

In an embodiment of the present disclosure, an administration dose of the pharmaceutical composition may be determined by a person with ordinary skill in the art in consideration of the purpose of use, severity of the disease, a patient's age, body weight, gender, medical history or the kind of a material used as an active ingredient. For example, the pharmaceutical composition of the present disclosure may be administered at a dose of from about 0.1 ng/kg to about 1,000 mg/kg and preferably, from about 1 ng/kg to about 100 mg/kg per adult, and the administration frequency of the composition of the present disclosure is not particularly limited, but the composition may be administered once a day or several times a day in divided doses. The administration dose or the administration frequency does not limit the scope of the present disclosure in any aspect.

A fourth aspect of the present disclosure provides a pharmaceutical composition for preventing or treating inflammatory diseases, including the anti-inflammatory peptide of the present disclosure as an active ingredient. The features described above in respect of the first to third aspects of the present disclosure may equally apply to the composition according to the fourth aspect of the present disclosure.

As used throughout the present disclosure, the term "treatment" refers to all activities capable of alleviating or ameliorating the symptoms of inflammatory diseases via administration of the composition according to the present disclosure.

As used throughout the present disclosure, the term "prevention" refers to all activities capable of inhibiting or delaying the onset of inflammatory disease or the possibility of its onset via administration of the composition according to the present disclosure.

As used throughout the present disclosure, the term "inflammatory disease" may be defined as pathological symptoms caused by an inflammatory response specified as a local or systemic defense response to infection with foreign infectious agents such as physical or chemical stimuli, bacteria, fungi, virus and various allergens or autoimmunity. The inflammatory response accompanies a series of complicated physiological responses including activation of various inflammatory mediators and immune cell related enzymes (for example, iNOS, COX-2, etc.), secretion of inflammatory mediators (for example, NO, TNF-α, IL-6, etc.), infiltration of body fluid, cell migration, tissue destruction, etc., and is shown as such symptoms as erythema, pain, edema, pyrexia, functional deficiency or loss, etc. The inflammatory disease can be acute, chronic, ulcerative, allergenic or necrotic. Therefore, as long as a disease is defined as the inflammatory disease, it does not matter whether it is acute, chronic, ulcerative, allergenic or necrotic.

In an embodiment of the present disclosure, the inflammatory disease may include at least one selected from the group consisting of sepsis, septic shock, systemic inflammatory response syndrome, acute respiratory distress syndrome, asthma, allergic and non-allergic rhinitis, chronic and acute rhinitis, chronic and acute gastritis or enteritis, ulcerative gastritis, acute and chronic nephritis, acute and chronic hepatitis, chronic obstructive pulmonary disease, idiopathic pulmonary fibrosis (IPF), irritable bowel syndrome, inflammatory pain, migraine, headache, lumbago, fibromyalgia, myofascial disease, viral infection (for example, hepatitis C), bacterial infection, fungal infection, burn, wound by surgical or dental operation, hyper-prostaglandin E syndrome, atherosclerosis, gout, arthritis, rheumatoid arthritis, ankylosing spondylitis, Hodgkin's disease, pancreatitis, conjunctivitis, iritis, scleritis, uveitis, dermatitis, atopic dermatitis, eczema, systemic lupus erythematosus (SLE) and multiple sclerosis, but is not limited thereto as long as it is a disease induced by an inflammatory response, specifically, a disease induced by an inflammatory response caused by a bacterial or viral infection.

A fifth aspect of the present disclosure provides a method for preventing or treating inflammation or inflammatory diseases, including administering to an individual the anti-inflammatory composition or the pharmaceutical composition for preventing or treating inflammatory diseases of the present disclosure. The features described above in respect of the first to fourth aspects of the present disclosure may equally apply to the method according to the fifth aspect of the present disclosure.

As used throughout the present disclosure, the term "subject" may include mammals including rats, livestock, humans, etc. and cultured fish which have or are at risk of developing an inflammatory response or inflammatory disease.

In an embodiment of the present disclosure, the subject may be other than a human.

In an embodiment of the present disclosure, the method may be performed administering a pharmaceutically effective amount of the composition to prevent or treat inflammation or inflammatory disease, and the administration amount may vary depending on various factors such as the degree of progression of an inflammatory response or inflammatory disease, a patient's age, body weight, characteristics and severity of symptoms, kinds of current treatment, the number of treatments, administration type and route and the like, and may be easily determined by experts in the corresponding art. The composition of the present disclosure may be administered together with pharmacological or physiological ingredients, or may be administered sequentially. Also, the composition of the present disclosure may be administered in combination with additional conventional therapeutic agent, and may be administered sequentially or simultaneously with the conventional therapeutic agents. Such administration may be single or multiple administration. It is important to administer the composition in the minimum amount that may exhibit the maximum effect without causing side-effects, in view of all of the above-described factors, and this may be easily determined by a person with ordinary skill in the art.

As used throughout the present disclosure, the term "administration" means an introduction of a predetermined material to a subject by any appropriate method. The composition of the present disclosure may be administered by any general route as long as the composition arrives at a target tissue. The administration may include intraperitoneal administration, intravenous administration, intramuscular administration, subcutaneous administration, intradermal administration, oral administration, topical administration, intranasal administration, intrapulmonary administration and intrarectal administration, but is not limited thereto. However, since protein is digested in the case of oral administration, an oral composition is preferred to be provided by coating an active agent thereon or to be formulated so as to protect the composition from being digested in the stomach. Further, the composition may be administered by any apparatus in which an active agent is movable to a target cell.

Hereinafter, the present disclosure will be explained in more detail with reference to Examples. However, the following Examples are illustrative only for better understanding of the present disclosure but do not limit the present disclosure.

MODE FOR CARRYING OUT THE INVENTION

Examples

Example 1: Synthesis of Novel Peptide with Anti-Inflammatory Effect

In order to develop anti-inflammatory peptides that can alleviate inflammatory responses by inhibiting the aggregation of mitochondrial anti-viral signaling (MAVS) proteins, which are known as major hub proteins in the innate immune response mechanism, an anti-inflammatory peptide sequence for inhibiting MAVS was derived by the following method.

Specifically, in the in vivo synthesis of a protein, a transcriptional RNA (mRNA) is made in the 5' to 3' direction of a DNA having a double helix structure, which results in the synthesis of a protein. However, it is known that when a new protein is synthesized by transcription of a complementary DNA sequence in another direction (3' to 5') in the direction in which an original protein is synthesized, the new protein has properties opposite to electrostatic properties of the original protein and specific binding occurs between them (hydropathic complementarity). Also, aggregation occurs at a stage when the MAVS protein is activated by external stimuli. Some sequences of the domains of the MAVS proteins, which are expected to play a key role in this stage, synthesize novel peptides complementary to the corresponding amino acid sequences based on the above-described hydropathic complementarity (SEQ ID NOS: 1 to 4, 48 to 52).

Example 2: Confirmation of Efficacy in Inhibiting MAVS Aggregation of Novel Peptide In order to confirm whether the novel peptides prepared in Example 1 are effective in inhibiting the aggregation of MAVS proteins, the following experiment was performed.

Specifically, the aggregation of MAVS proteins was induced by stimulation with pathogen-associated molecular patterns (PAMPs), and endotoxin (lipopolysaccharide (LPS)) and nigericin were used as the PAMPs. First, 5 mM MQP-15, MQP-23, MQP-31 or MQP-37 was added to a serum-free cell culture medium containing 1 mg/ml LPS, followed by treatment with $1\times10^5$ cells of a mouse peritoneal macrophage cell line (IC21) for 4 hours. Then, 5 mM MQP-15, MQP-23, MQP-31 or MQP-37 was added to a serum-free cell culture medium containing 5 mM nigericin, followed by treatment with IC21 for additional 1 hour. Thereafter, mitochondria in IC21 were isolated with a hypotonic buffer and centrifugation. Then, in order to check the result of MAVS aggregation by the Western blot, a sample was prepared using a semi-denaturing detergent in the isolated mitochondria and electrophoresis was performed. After the electrophoretically isolated mitochondrial protein was transferred to a polyvinylidene difluoride (PVDF) membrane, a primary antibody recognizing the MAVS proteins and a secondary antibody recognizing the primary antibody were additionally treated. Thereafter, the aggregation of MAVS proteins was checked by inducing a chemiluminescence reaction of the secondary antibody.

As a result, it was confirmed that the aggregation of MAVS proteins found in the control group treated with endotoxin and nigericin was decreased in the experimental group treated with MQP-15, MQP-23, MQP-31 or MQP-37 (FIG. 2). Thus, it can be seen that MQP-15, MQP-23, MQP-31 or MQP-37 prepared in the present disclosure effectively inhibits the aggregation of MAVS proteins.

Example 3: Confirmation of Efficacy in Inhibiting Antiviral Response of Novel Peptide In order to confirm whether the novel peptides prepared in Example 1 are effective in inhibiting an antiviral response caused by viral infection, the following experiment was performed.

Specifically, polyinosinic:polycytidylic acid (polyIC), which is a synthetic ribonucleic acid known to be associated with viral infection among the PAMPs and promotes the production of interferon and is analogous to an RNA virus gene, was used to induce a viral infection response. First, a serum-free cell culture medium containing 5 mg/ml polyIC and MQP-15, MQP-23, MQP-31, MQP-37, MQP-Y9 or MQP-T234 was treated with $1\times10^5$ cells of a mouse lung epithelial cell line (MLE-12) for 16 hours. Then, the supernatant was obtained and the expression level of interferon-beta (IFN-b) was checked by enzyme-linked immunosorbent assay (ELISA).

As a result, it was confirmed that the expression level of IFN-b was decreased in case of treatment with MQP-15, MQP-23, MQP-31, MQP-37, MQP-Y9 or MQP-T234, compared to the control group treated only with polyIC. In particular, it was confirmed that MQP-37 more significantly decreased the expression level of IFN-b than the other peptides (FIG. 3A-A). Also, as a result of performing the same experiment as described above with various concentrations of MQP-37 having excellent effect, it was confirmed that the expression level of IFN-b was decreased in a concentration-dependent manner (FIG. 3A-B). As a result of performing the same experiment as described above with various concentrations of MQP-Y9, it was confirmed that the expression level of IFN-b was decreased in a concentration-dependent manner (FIG. 3B-C). In the same experiment treated with MQP-T234, the expression level of IFN-b was decreased (FIG. 3B-D). Based on the above results, it can be seen that MQP-15, MQP-23, MQP-31, MQP-37, MQP-Y9 or MQP-T234 produced in the present disclosure effectively inhibits the antiviral response caused by viral infection.

Example 4: Identification of Cytotoxicity of Novel Peptide

In order to confirm whether the inflammation inhibitory effect of the novel peptides prepared in Example 1 is the result of cytotoxicity of the peptides themselves, the following experiment was performed.

Specifically, in order to check the cytotoxicity of the peptides, the XTT test method for measuring the activity of mitochondria in cells was used. First, a serum-free cell culture medium containing 5 mM MQP-15, MQP-23, MQP-31 or MQP-37 was treated with IC21 for 16 hours, followed by XTT assay for 1 hour to measure the amount of water-soluble formazan produced by reduction by dehydrogenase in the mitochondria.

As a result, it was confirmed that the cytotoxicity of the novel peptides of the present disclosure did not appear in the concentration range used in the cell experiment (FIG. 4-A). In particular, it was confirmed that MQP-37 and MQP-Y9 found as peptides that very effectively inhibit the inflammatory response caused by polyIC did not exhibit any cytotoxicity even at a concentration of 10 mM (FIGS. 4-B and 4-C). Therefore, it can be seen that the inflammation inhibitory effect is not due to cytotoxicity of the peptides themselves and the peptides are not harmful to a subject even when used as drugs.

Example 5: Confirmation of Efficacy in Inhibiting Inflammasome Response of Novel Peptide In order to confirm whether the novel peptides prepared in Example 1 are effective in inhibiting an inflammasome response caused by bacterial infection, the following experiment was performed.

Specifically, LPS (lipopolysaccharide) and Gram-negative bacteria-derived outer membrane vesicle (OMV) were used as endotoxins to induce the inflammasome response caused by bacterial infection. First, 5 mM MQP-15, MQP-23, MQP-31 or MQP-37 was added to a serum-free cell culture medium containing 0.1 mg/ml LPS or OMV, followed by treatment with $1\times10^5$ cells of IC21 for 6 hours. Also, MQP-37 or MQP-Y9 was added to a serum-free cell culture medium containing 1 mg/ml LPS and 5 mM nigericin, followed by treatment for 5 hours (LPS treatment-4 hours; nigericin treatment-1 hour). Then, the supernatant was obtained and the expression level of interleukin-1beta (IL-1b) was checked by ELISA, and the cells were lysed and subjected to SDS-PAGE, and the inflammasome factors were analyzed by the Western blot.

As a result, it was confirmed that the expression level of IL-1b was decreased in case of treatment with the novel peptides of the present disclosure, compared to the control group treated with LPS or OMV only. In particular, it was confirmed that MQP-37 more significantly decreased the expression level of IL-1b than the other peptides (FIG. 5A-A and FIG. 5B-C). Also, as a result of performing the same experiment as described above with various concentrations of MQP-37 having excellent effect, it was confirmed that the expression level of IL-1b after LPS treatment was decreased in a concentration-dependent manner (FIG. 5A-B). It was confirmed that the production of IL-1b after LPS and nigericin treatment was inhibited in an MQP-Y9 concentration-dependent manner (FIG. 5B-D). Further, it was confirmed that the activation of caspase-1 was inhibited by MQP-37 treatment (FIG. 5C-E). Based on the above results, it can be seen that the novel peptides prepared in the present disclosure effectively inhibit the inflammasome response caused by bacterial infection.

Example 6: Confirmation of Efficacy in Inflammatory Response of Novel Peptide In order to confirm whether the novel peptides prepared in Example 1 are effective in inhibiting an inflammatory response, the following experiment was performed.

Specifically, LPS was used to induce an inflammatory response caused by bacterial infection. First, MQP-15, MQP-23, MQP-31, MQP-37 or MQP-Y9 was added to a serum-free cell culture medium containing 0.1 mg/ml LPS, followed by treatment with $1\times10^5$ cells of IC21 for 6 hours. Then, the supernatant was obtained and the expression levels of interleukin-6 (IL-6) and a tumor necrosis factor-alpha (TNF-a) were checked by ELISA.

As a result, it was confirmed that the expression levels of IL-6 and TNF-a were significantly decreased in case of treatment with MQP-37 among the novel peptides of the present disclosure, compared to the control group treated with LPS only (FIG. 6A-A and FIG. 6B-C). Also, as a result of performing the same experiment as described above with various concentrations of MQP-37 having excellent effect, it was confirmed that the expression level of IL-6 after LPS treatment was decreased in a concentration-dependent manner (FIG. 6A-B). As a result of performing the same experiment as described above with various concentrations of MQP-Y9, it was confirmed that the expression level of IL-6 after LPS treatment was decreased in a concentration-dependent manner (FIG. 6B-D). Based on the above results, it can be seen that the novel peptides prepared in the present disclosure effectively inhibit the inflammatory response.

Example 7: Confirmation of Efficacy in Inhibiting Mechanism of Mechanism of Immune Activation Response of Novel Peptide In order to confirm whether the novel peptides prepared in Example 1 are effective in inhibiting the mechanism of immune activation response, the following experiment was performed.

Specifically, LPS was used to induce an immune activation response caused by bacterial infection, and the phosphorylation of nuclear factor kappa-light-chain-enhancer of activated B cells (NF-kB) was checked to identify the mechanism of the immune activation response. First, 5 mM MQP-15, MQP-23, MQP-31, MQP-37, MQP-Y9, MQP-91, MQP-T234 or MQP-341 was added to a serum-free cell culture medium containing 10 ng/ml endotoxin, followed by treatment with $1\times10^6$ cells of IC21 for 6 hours. Thereafter, the cells were washed with a PBS solution and then lysed with a RIPA buffer, and the supernatant was separated. In order to measure the change in the phosphorylation amount of NF-κB protein with the separated supernatant, the Western blot was performed as in Example 2.

As a result, it was confirmed that the phosphorylation amount of NF-κB was significantly decreased in case of treatment with MQP-37 and MQP-Y9 among the novel peptides of the present disclosure, compared to the control group treated with LPS only (FIG. 7). Based on the above result, it can be seen that the novel peptides prepared in the present disclosure effectively inhibit the mechanism of immune activation response.

Example 8: Confirmation of Improvement in Protease Resistance of Novel D-Peptide A D-amino acid was synthesized to improve a protease resistance of the novel peptide MQP-37 whose anti-inflammatory activity was confirmed through the experiments of from Example 2 to Example 7, and the following experiment was performed to check the protease resistance.

Specifically, LPS was used to induce an inflammatory response caused by bacterial infection. First, 0.1 mg/ml LPS was mixed in a serum-free cell culture medium or a 10% fetal bovine serum (FBS) cell culture medium. Then, 5 mM L-peptide MQP-37 and 5 mM D-peptide MQP-37 were added to each cell culture medium containing LPS, followed by treatment with $1\times10^5$ cells of IC21 for 6 hours. Thereafter, the supernatant was obtained and expression levels of IL-6 and TNF-a were checked by ELISA.

As a result, it was confirmed that both of the novel L- and D-peptides of the present disclosure exhibited the same anti-inflammatory response in the serum-free cell culture medium in the absence of a protease, compared to the control treated with LP only. However, it was confirmed that in the 10% FBS cell culture medium in the presence of a protease, the novel L-peptide of the present disclosure did not exhibit anti-inflammatory activity, whereas the novel D-peptide still exhibited anti-inflammatory activity (FIG. 8). Based on the above results, it can be seen that the novel D-peptide prepared in the present disclosure effectively inhibits the inflammatory response regardless of the presence or absence of a protease.

Example 9: Confirmation of Improvement in Anti-Inflammatory Effect of Novel Alanine-Substituted Peptide Peptides in which each sequence was sequentially substituted with alanine were synthesized to identify key amino acids of the novel peptides MQP-37 and MQP-Y9 whose anti-inflammatory activity was confirmed through the experiments of from Example 2 to Example 8 (MQP-37 alanine-substituted peptides [MQP-37 derivatives]-SEQ ID NOS: 5 to 11; MQP-Y9 alanine-substituted peptides [MQP-Y9 derivatives]-SEQ ID NOS: 53 to 62), and the following experiment was performed to check the anti-inflammatory effect.

Specifically, LPS and ATP were used to induce an inflammasome response caused by bacterial infection, and polyIC was used to induce an inflammatory response caused by viral infection. First, 1 mg/ml LPS and 5 mM or 1 mM novel alanine-substituted peptide were mixed in a serum-free cell culture medium, followed by treatment with $1\times10^5$ cells of IC21. Thereafter, 5 mM ATP and 5 mM or 1 mM novel alanine-substituted peptide were mixed in a serum-free cell culture medium and treated for 30 minutes. Then, the supernatant was obtained and the expression level of IL-1b was checked by ELISA. Also, 5 mg/ml polyIC and 25 mM or 2 mM novel alanine-substituted peptide were mixed in a serum-free cell culture medium, followed by treatment with $1\times10^5$ cells of MLE-12 for 16 hours. Thereafter, the supernatant was obtained and the expression level of IFN-b was checked by ELISA.

As a result, it was confirmed that MQP-37 whose first and sixth amino acids were substituted with alanine (A1 and A6)

significantly improved the inflammasome response caused by bacterial infection and the inflammatory response caused by viral infection, compared to the original MQP-37 peptide (FIGS. 9A-A and 9A-B). Also, it was confirmed that MQP-Y9 whose second, seventh and ninth amino acids were substituted with alanine (A2, A7 and A9) inhibited the inflammasome response caused by bacterial infection and exhibited excellent anti-inflammatory response, compared to the original MQP-Y9 (FIG. 9B-C). Further, it was confirmed that MQP-Y9 whose tenth amino acid was substituted with alanine (A10) more effectively inhibited the inflammatory response caused by viral infection than the original MQP-Y9 (FIG. 9C-D). Based on the above results, it can be seen that the novel alanine-substituted peptides prepared in the present disclosure effectively inhibit the inflammasome response caused by bacterial infection and the inflammatory response caused by viral infection (SEQ ID NOS: 5 to 11; 53 to 62).

Example 10: Confirmation of Anti-Inflammatory Effect of Novel Peptides in which First and Sixth Amino Acid Sequences are Substituted with Other Amino Acids The first position of the novel peptide MQP-37A6 (SEQ ID NO: 9) whose anti-inflammatory effect was confirmed through the experiment of Example 9 was substituted with 19 amino acids to synthesize MQP-37A1 derivatives (SEQ ID NOS: 12 to 29 and 63). Also, the sixth position of MQP-37A6 was substituted with 18 amino acids except aspartic acid to synthesize MQP-37A6 derivatives (SEQ ID NOS: 30 to 47). The following experiment was performed to confirm whether the peptides are effective in improving the anti-inflammatory effect.

Specifically, LPS and ATP were used to induce an inflammasome response caused by bacterial infection, and polyIC was used to induce an inflammatory response caused by viral infection. First, 1 mg/ml LPS and 2 mM novel amino acid-substituted peptide were mixed in a serum-free cell culture medium, followed by treatment with $1\times10^5$ cells of IC21. Thereafter, 5 mM ATP and 2 mM novel amino acid-substituted peptide were mixed in a serum-free cell culture medium and treated for 30 minutes. Then, the supernatant was obtained and the expression level of IL-1b was checked by ELISA. Also, 5 mg/ml polyIC and 2 mM novel amino acid-substituted peptide were mixed in a serum-free cell culture medium, followed by treatment with $1\times10^5$ cells of MLE-12 for 16 hours. Thereafter, the supernatant was obtained and the expression level of IFN-b was checked by ELISA.

As a result, it was confirmed that MQP-37A1 prepared by substituting the first amino acid of MQP-37A6 with alanine inhibited the inflammasome response caused by bacterial infection most effectively, and the peptides substituted with phenylalanine (F), leucine (L), arginine (R) and tyrosine (Y) also inhibited the inflammasome response caused by bacterial infection effectively (FIG. 10A-A). Also, it was confirmed that when the sixth amino acid of MQP-37 was substituted with other amino acids, alanine (A), phenylalanine (F), histidine (H), leucin (L) and methionine (M) inhibited the inflammasome response caused by bacterial infection effectively as shown in FIG. 10A-B, and in particular, the novel peptide substituted with alanine inhibited the inflammasome response caused by bacterial infection most effectively. It was confirmed that when the sixth amino acid of MQP-37 is substituted with tryptophan (W) or tyrosine (Y), the inflammatory response caused by viral infection was effectively inhibited even at a low peptide concentration, compared to the original peptide (FIG. 10B-C). Based on the above results, it can be seen that the novel amino acid-substituted peptides prepared in the present disclosure effectively inhibit the inflammasome response caused by bacterial infection and the inflammatory response caused by viral infection.

Example 11: Comparison of Binding Affinity Between Novel Peptide MQP-37 and Novel Alanine-Substituted Peptide MQP-37A6

The following experiment was performed to compare the binding affinity of the novel alanine-substituted peptide MQP-37A6 whose anti-inflammatory activity was confirmed through the experiments of from Example 9 to Example 10 to the MAVS protein with that of the original peptide MQP-37.

Specifically, recombinant MAVS protein and fluorescence-labeled peptides MQP-37 and MQP-37A6 were used to check the binding affinity to the MAVS protein. First, 250 ng of recombinant MAVS protein was coated on a 96-well plate for ELISA, followed by blocking with 1% BSA/PBS solution. Thereafter, fluorescence-labeled peptides of various concentrations were added thereto and reacted for 2 hours, and the amount of peptide bound to the MAVS protein was checked by fluorescence measurement.

As a result, when the binding affinity to the MAVS protein was measured by treatment with MQP-37 at different concentrations, the binding affinity ($K_d$) was measured to be about 16 mM, which was confirmed to have a strong binding affinity about 20 times higher than the case of treatment with MQP-37A6 in which the binding affinity was measured to be about 0.75 mM (FIG. 11). Based on the above result, it can be seen that the novel peptide MQP-37A6 prepared in the present disclosure has an improved binding affinity to the MAVS protein.

Example 12: Comparison of Physiological Activity Between Novel Peptide MQP-37 and Novel Alanine-Substituted Peptide MQP-37A6

The following experiment was performed to compare the physiological activity of the novel alanine-substituted peptide MQP-37A6 whose anti-inflammatory activity was confirmed through the experiments of from Example 9 to Example 10 with that of the original peptide MQP-37.

Specifically, LPS was used to induce an inflammatory response caused by bacterial infection. First, MQP-37 or MQP-37A6 was added to a serum-free cell culture medium containing 0.1 mg/ml LPS, followed by treatment with $1\times10^5$ cells of IC21 for 6 hours. Then, the supernatant was obtained and the expression level of IL-6 was checked by ELISA. Also, the Western blot was performed and the phosphorylation of NF-κB was checked to identify the mechanism of immune activation response. Thereafter, LPS and ATP were used to induce an inflammasome response caused by bacterial infection, LPS and ATP were used. First, 1 mg/ml LPS and L- or D-MQP-37 and MQP-37A6 were mixed in a serum-free cell culture medium and treated with $1\times10^5$ cells of IC21. Then, 5 mM ATP and MQP-37 or MQP-37A6 were mixed in a serum-free cell culture medium and treated for 30 minutes. Thereafter, the supernatant was obtained and the expression level of IL-1b was checked by ELISA.

As a result, it was confirmed that L- and D-MQP-37A6 whose sixth amino acid was substituted with alanine inhibited the inflammatory response (FIG. 12A-A) and inflammasome response (FIGS. 12A-B and 12A-C) caused by bacterial infection and the immune activation response (NF-κB phosphorylation, FIGS. 12B-D to 12B-F) more than the original peptide MQP-37. Based on the above results, it can be seen that the novel alanine-substituted peptide (MQP-37A6) prepared in the present disclosure effectively inhibits the inflammatory response.

Example 13: Comparison of Viral Inflammatory Response Between Novel Peptide MQP-37 and Novel Amino Acid-Substituted Peptides MQP-37D6Y, MQP-37D6W, MQP-37D6H The following experiment was performed to compare the activity of the new amino acid-substituted peptides MQP-37D6Y and MQP-37D6W whose activity of inhibiting a viral inflammatory response was confirmed through the experiment of Example 10 with that of the original peptide MQP-37.

Specifically, polyIC was used to induce a viral infection response. First, a serum-free cell culture medium containing 5 mg/ml polyIC and MQP-37, MQP-37A6, MQP-37D6W, MQP-37D6Y, MQP-37D6H, MQP-37D6K, MQP-37D6R or MQP-37D6V was treated with $1\times10^5$ cells of MLE-12 for 16 hours. Then, the supernatant was obtained and the expression level of IFN-b was checked by ELISA.

As a result, it was confirmed that MQP-37D6W and MQP-37D6Y exhibited outstanding effect of inhibiting the inflammatory response caused by viral infection in a concentration-dependent manner, compared to MQP-37 and MQP-37A6 (FIGS. 13A-A and 13A-B). Also, it was confirmed that MQP-37D6Y inhibited polyIC-induced apoptosis effectively (FIG. 13B-E) and it did not show cytotoxicity at the maximum concentration thereof in the experiment (FIG. 13B-F). Further, it was confirmed that MQP-37D6H inhibited the inflammatory response caused by viral infection in a concentration-dependent manner (FIGS. 13A-C and 13A-D). Based on the above results, it can be seen that the novel amino acid-substituted peptides including MQP-37D6Y prepared in the present disclosure effectively inhibit the inflammatory response caused by viral infection.

Example 14: Confirmation of Effect of Novel Peptide in Mouse Sepsis Model

The following experiment was performed to check the effect of D- or L-MQP-37 and MQP-37A6 whose activity of inhibiting an inflammatory response caused by bacterial infection was confirmed through the experiments of from Example 2 to Example 12 on a mouse sepsis model.

Specifically, 2 mg/kg and 5 mg/kg LPS were administered into the abdominal cavity of 7-week-old C57BL/6 wild-type mice every 6 hours, and 1 hour later, 0.4 mg/kg, 2 mg/kg and 10 mg/kg novel peptides were additionally administered into the abdominal cavity of the mice. Then, the survival of the mice was checked for 4 days.

As a result, it was confirmed in case of administration of 0.4 mg/kg, the survival rate was from 40% to 80% and in case of administration of 2 mg/kg and 10 mg/kg, 100% of the mice survived (FIGS. 14-A to 14-C). Also, it was confirmed that the amount of IL-6, which is an inflammatory cytokine, in the blood was decreased in the group treated with the novel peptide, compared to the control group (FIG. 14-D). Based on the above results, it can be seen that D- or L-MQP-37 and MQP-37A6 are effective in treating sepsis, which is an inflammatory disease.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. An anti-inflammatory peptide consisting of an amino acid sequence selected from the group consisting of SEQ ID NOs: 12, 17, 18, 29, 34, 35, 38, 41, 43, 44, and 46.

2. An anti-inflammatory composition, comprising:

(a) an anti-inflammatory peptide of claim 1; and (b) a pharmaceutically acceptable carrier.

3. A pharmaceutical composition for preventing or treating inflammatory diseases, comprising:

(a) an anti-inflammatory peptide of claim 1; and (b) a pharmaceutically acceptable carrier.

* * * * *

SEQUENCE LISTING

```
<160> NUMBER OF SEQ ID NOS: 63

<210> SEQ ID NO 1
<211> LENGTH: 8
<212> TYPE: PRT
<213> ORGANISM: Artificial Sequence
<220> FEATURE:
<223> OTHER INFORMATION: MQP-15

<400> SEQUENCE: 1

Leu Lys Ser Leu Lys Thr Leu His
1               5


<210> SEQ ID NO 2
<211> LENGTH: 8
<212> TYPE: PRT
<213> ORGANISM: Artificial Sequence
<220> FEATURE:
<223> OTHER INFORMATION: MQP-23

<400> SEQUENCE: 2

Leu Gln His Leu Glu Asp Gly Met
```

1 5

<210> SEQ ID NO 3
<211> LENGTH: 6
<212> TYPE: PRT
<213> ORGANISM: Artificial Sequence
<220> FEATURE:
<223> OTHER INFORMATION: MQP-31

<400> SEQUENCE: 3

Asp Gly Thr Glu Cys Arg
1 5

<210> SEQ ID NO 4
<211> LENGTH: 9
<212> TYPE: PRT
<213> ORGANISM: Artificial Sequence
<220> FEATURE:
<223> OTHER INFORMATION: MQP-37

<400> SEQUENCE: 4

Ser Leu Val Leu Ala Asp Ala Arg Trp
1 5

<210> SEQ ID NO 5
<211> LENGTH: 9
<212> TYPE: PRT
<213> ORGANISM: Artificial Sequence
<220> FEATURE:
<223> OTHER INFORMATION: MQP-37A1

<400> SEQUENCE: 5

Ala Leu Val Leu Ala Asp Ala Arg Trp
1 5

<210> SEQ ID NO 6
<211> LENGTH: 9
<212> TYPE: PRT
<213> ORGANISM: Artificial Sequence
<220> FEATURE:
<223> OTHER INFORMATION: MQP-37A2

<400> SEQUENCE: 6

Ser Ala Val Leu Ala Asp Ala Arg Trp
1 5

<210> SEQ ID NO 7
<211> LENGTH: 9
<212> TYPE: PRT
<213> ORGANISM: Artificial Sequence
<220> FEATURE:
<223> OTHER INFORMATION: MQP-37A3

<400> SEQUENCE: 7

Ser Leu Ala Leu Ala Asp Ala Arg Trp
1 5

<210> SEQ ID NO 8
<211> LENGTH: 9
<212> TYPE: PRT
<213> ORGANISM: Artificial Sequence
<220> FEATURE:
<223> OTHER INFORMATION: MQP-37A4

<400> SEQUENCE: 8

Ser Leu Val Ala Ala Asp Ala Arg Trp
1 5

<210> SEQ ID NO 9
<211> LENGTH: 9
<212> TYPE: PRT
<213> ORGANISM: Artificial Sequence
<220> FEATURE:
<223> OTHER INFORMATION: MQP-37A6

<400> SEQUENCE: 9

Ser Leu Val Leu Ala Ala Ala Arg Trp
1 5

<210> SEQ ID NO 10
<211> LENGTH: 9
<212> TYPE: PRT
<213> ORGANISM: Artificial Sequence
<220> FEATURE:
<223> OTHER INFORMATION: MQP-37A8

<400> SEQUENCE: 10

Ser Leu Val Leu Ala Asp Ala Ala Trp
1 5

<210> SEQ ID NO 11
<211> LENGTH: 9
<212> TYPE: PRT
<213> ORGANISM: Artificial Sequence
<220> FEATURE:
<223> OTHER INFORMATION: MQP-37A9

<400> SEQUENCE: 11

Ser Leu Val Leu Ala Asp Ala Arg Ala
1 5

<210> SEQ ID NO 12
<211> LENGTH: 9
<212> TYPE: PRT
<213> ORGANISM: Artificial Sequence
<220> FEATURE:
<223> OTHER INFORMATION: MQP-37S1C

<400> SEQUENCE: 12

Cys Leu Val Leu Ala Ala Ala Arg Trp
1 5

<210> SEQ ID NO 13
<211> LENGTH: 9
<212> TYPE: PRT
<213> ORGANISM: Artificial Sequence
<220> FEATURE:
<223> OTHER INFORMATION: MQP-37S1D

<400> SEQUENCE: 13

Asp Leu Val Leu Ala Ala Ala Arg Trp
1 5

<210> SEQ ID NO 14
<211> LENGTH: 9
<212> TYPE: PRT
<213> ORGANISM: Artificial Sequence
<220> FEATURE:
<223> OTHER INFORMATION: MQP-37S1E

<400> SEQUENCE: 14

Glu Leu Val Leu Ala Ala Ala Arg Trp
1 5

<210> SEQ ID NO 15
<211> LENGTH: 9
<212> TYPE: PRT
<213> ORGANISM: Artificial Sequence
<220> FEATURE:
<223> OTHER INFORMATION: MQP-37S1F

<400> SEQUENCE: 15

Phe Leu Val Leu Ala Ala Ala Arg Trp
1               5

<210> SEQ ID NO 16
<211> LENGTH: 9
<212> TYPE: PRT
<213> ORGANISM: Artificial Sequence
<220> FEATURE:
<223> OTHER INFORMATION: MQP-37S1G

<400> SEQUENCE: 16

Gly Leu Val Leu Ala Ala Ala Arg Trp
1               5

<210> SEQ ID NO 17
<211> LENGTH: 9
<212> TYPE: PRT
<213> ORGANISM: Artificial Sequence
<220> FEATURE:
<223> OTHER INFORMATION: MQP-37S1H

<400> SEQUENCE: 17

His Leu Val Leu Ala Ala Ala Arg Trp
1               5

<210> SEQ ID NO 18
<211> LENGTH: 9
<212> TYPE: PRT
<213> ORGANISM: Artificial Sequence
<220> FEATURE:
<223> OTHER INFORMATION: MQP-37S1I

<400> SEQUENCE: 18

Ile Leu Val Leu Ala Ala Ala Arg Trp
1               5

<210> SEQ ID NO 19
<211> LENGTH: 9
<212> TYPE: PRT
<213> ORGANISM: Artificial Sequence
<220> FEATURE:
<223> OTHER INFORMATION: MQP-37S1K

<400> SEQUENCE: 19

Lys Leu Val Leu Ala Ala Ala Arg Trp
1               5

<210> SEQ ID NO 20
<211> LENGTH: 9
<212> TYPE: PRT
<213> ORGANISM: Artificial Sequence
<220> FEATURE:
<223> OTHER INFORMATION: MQP-37S1L

<400> SEQUENCE: 20

Leu Leu Val Leu Ala Ala Ala Arg Trp
1               5

<210> SEQ ID NO 21
<211> LENGTH: 9
<212> TYPE: PRT
<213> ORGANISM: Artificial Sequence
<220> FEATURE:
<223> OTHER INFORMATION: MQP-37S1M

<400> SEQUENCE: 21

Met Leu Val Leu Ala Ala Ala Arg Trp
1 5

<210> SEQ ID NO 22
<211> LENGTH: 9
<212> TYPE: PRT
<213> ORGANISM: Artificial Sequence
<220> FEATURE:
<223> OTHER INFORMATION: MQP-37S1N

<400> SEQUENCE: 22

Asn Leu Val Leu Ala Ala Ala Arg Trp
1 5

<210> SEQ ID NO 23
<211> LENGTH: 9
<212> TYPE: PRT
<213> ORGANISM: Artificial Sequence
<220> FEATURE:
<223> OTHER INFORMATION: MQP-37S1P

<400> SEQUENCE: 23

Pro Leu Val Leu Ala Ala Ala Arg Trp
1 5

<210> SEQ ID NO 24
<211> LENGTH: 9
<212> TYPE: PRT
<213> ORGANISM: Artificial Sequence
<220> FEATURE:
<223> OTHER INFORMATION: MQP-37S1Q

<400> SEQUENCE: 24

Gln Leu Val Leu Ala Ala Ala Arg Trp
1 5

<210> SEQ ID NO 25
<211> LENGTH: 9
<212> TYPE: PRT
<213> ORGANISM: Artificial Sequence
<220> FEATURE:
<223> OTHER INFORMATION: MQP-37S1R

<400> SEQUENCE: 25

Arg Leu Val Leu Ala Ala Ala Arg Trp
1 5

<210> SEQ ID NO 26
<211> LENGTH: 9
<212> TYPE: PRT
<213> ORGANISM: Artificial Sequence
<220> FEATURE:
<223> OTHER INFORMATION: MQP-37S1T

<400> SEQUENCE: 26

Thr Leu Val Leu Ala Ala Ala Arg Trp
1 5

<210> SEQ ID NO 27

<211> LENGTH: 9
<212> TYPE: PRT
<213> ORGANISM: Artificial Sequence
<220> FEATURE:
<223> OTHER INFORMATION: MQP-37S1V

<400> SEQUENCE: 27

Val Leu Val Leu Ala Ala Ala Arg Trp
1 5

<210> SEQ ID NO 28
<211> LENGTH: 9
<212> TYPE: PRT
<213> ORGANISM: Artificial Sequence
<220> FEATURE:
<223> OTHER INFORMATION: MQP-37S1W

<400> SEQUENCE: 28

Trp Leu Val Leu Ala Ala Ala Arg Trp
1 5

<210> SEQ ID NO 29
<211> LENGTH: 9
<212> TYPE: PRT
<213> ORGANISM: Artificial Sequence
<220> FEATURE:
<223> OTHER INFORMATION: MQP-37S1Y

<400> SEQUENCE: 29

Tyr Leu Val Leu Ala Ala Ala Arg Trp
1 5

<210> SEQ ID NO 30
<211> LENGTH: 9
<212> TYPE: PRT
<213> ORGANISM: Artificial Sequence
<220> FEATURE:
<223> OTHER INFORMATION: MQP-37D6C

<400> SEQUENCE: 30

Ser Leu Val Leu Ala Cys Ala Arg Trp
1 5

<210> SEQ ID NO 31
<211> LENGTH: 9
<212> TYPE: PRT
<213> ORGANISM: Artificial Sequence
<220> FEATURE:
<223> OTHER INFORMATION: MQP-37D6E

<400> SEQUENCE: 31

Ser Leu Val Leu Ala Glu Ala Arg Trp
1 5

<210> SEQ ID NO 32
<211> LENGTH: 9
<212> TYPE: PRT
<213> ORGANISM: Artificial Sequence
<220> FEATURE:
<223> OTHER INFORMATION: MQP-37D6F

<400> SEQUENCE: 32

Ser Leu Val Leu Ala Phe Ala Arg Trp
1 5

<210> SEQ ID NO 33
<211> LENGTH: 9

<212> TYPE: PRT
<213> ORGANISM: Artificial Sequence
<220> FEATURE:
<223> OTHER INFORMATION: MQP-37D6G

<400> SEQUENCE: 33

Ser Leu Val Leu Ala Gly Ala Arg Trp
1               5

<210> SEQ ID NO 34
<211> LENGTH: 9
<212> TYPE: PRT
<213> ORGANISM: Artificial Sequence
<220> FEATURE:
<223> OTHER INFORMATION: MQP-37D6H

<400> SEQUENCE: 34

Ser Leu Val Leu Ala His Ala Arg Trp
1               5

<210> SEQ ID NO 35
<211> LENGTH: 9
<212> TYPE: PRT
<213> ORGANISM: Artificial Sequence
<220> FEATURE:
<223> OTHER INFORMATION: MQP-37D6I

<400> SEQUENCE: 35

Ser Leu Val Leu Ala Ile Ala Arg Trp
1               5

<210> SEQ ID NO 36
<211> LENGTH: 9
<212> TYPE: PRT
<213> ORGANISM: Artificial Sequence
<220> FEATURE:
<223> OTHER INFORMATION: MQP-37D6K

<400> SEQUENCE: 36

Ser Leu Val Leu Ala Lys Ala Arg Trp
1               5

<210> SEQ ID NO 37
<211> LENGTH: 9
<212> TYPE: PRT
<213> ORGANISM: Artificial Sequence
<220> FEATURE:
<223> OTHER INFORMATION: MQP-37D6L

<400> SEQUENCE: 37

Ser Leu Val Leu Ala Leu Ala Arg Trp
1               5

<210> SEQ ID NO 38
<211> LENGTH: 9
<212> TYPE: PRT
<213> ORGANISM: Artificial Sequence
<220> FEATURE:
<223> OTHER INFORMATION: MQP-37D6M

<400> SEQUENCE: 38

Ser Leu Val Leu Ala Met Ala Arg Trp
1               5

<210> SEQ ID NO 39
<211> LENGTH: 9
<212> TYPE: PRT

<213> ORGANISM: Artificial Sequence
<220> FEATURE:
<223> OTHER INFORMATION: MQP-37D6N

<400> SEQUENCE: 39

Ser Leu Val Leu Ala Asn Ala Arg Trp
1               5

<210> SEQ ID NO 40
<211> LENGTH: 9
<212> TYPE: PRT
<213> ORGANISM: Artificial Sequence
<220> FEATURE:
<223> OTHER INFORMATION: MQP-37D6P

<400> SEQUENCE: 40

Ser Leu Val Leu Ala Pro Ala Arg Trp
1               5

<210> SEQ ID NO 41
<211> LENGTH: 9
<212> TYPE: PRT
<213> ORGANISM: Artificial Sequence
<220> FEATURE:
<223> OTHER INFORMATION: MQP-37D6Q

<400> SEQUENCE: 41

Ser Leu Val Leu Ala Gln Ala Arg Trp
1               5

<210> SEQ ID NO 42
<211> LENGTH: 9
<212> TYPE: PRT
<213> ORGANISM: Artificial Sequence
<220> FEATURE:
<223> OTHER INFORMATION: MQP-37D6R

<400> SEQUENCE: 42

Ser Leu Val Leu Ala Arg Ala Arg Trp
1               5

<210> SEQ ID NO 43
<211> LENGTH: 9
<212> TYPE: PRT
<213> ORGANISM: Artificial Sequence
<220> FEATURE:
<223> OTHER INFORMATION: MQP-37D6S

<400> SEQUENCE: 43

Ser Leu Val Leu Ala Ser Ala Arg Trp
1               5

<210> SEQ ID NO 44
<211> LENGTH: 9
<212> TYPE: PRT
<213> ORGANISM: Artificial Sequence
<220> FEATURE:
<223> OTHER INFORMATION: MQP-37D6T

<400> SEQUENCE: 44

Ser Leu Val Leu Ala Thr Ala Arg Trp
1               5

<210> SEQ ID NO 45
<211> LENGTH: 9
<212> TYPE: PRT
<213> ORGANISM: Artificial Sequence

```
<220> FEATURE:
<223> OTHER INFORMATION: MQP-37D6V

<400> SEQUENCE: 45

Ser Leu Val Leu Ala Val Ala Arg Trp
1               5


<210> SEQ ID NO 46
<211> LENGTH: 9
<212> TYPE: PRT
<213> ORGANISM: Artificial Sequence
<220> FEATURE:
<223> OTHER INFORMATION: MQP-37D6W

<400> SEQUENCE: 46

Ser Leu Val Leu Ala Trp Ala Arg Trp
1               5


<210> SEQ ID NO 47
<211> LENGTH: 9
<212> TYPE: PRT
<213> ORGANISM: Artificial Sequence
<220> FEATURE:
<223> OTHER INFORMATION: MQP-37D6Y

<400> SEQUENCE: 47

Ser Leu Val Leu Ala Tyr Ala Arg Trp
1               5


<210> SEQ ID NO 48
<211> LENGTH: 10
<212> TYPE: PRT
<213> ORGANISM: Artificial Sequence
<220> FEATURE:
<223> OTHER INFORMATION: MQP-Y9

<400> SEQUENCE: 48

Lys Arg Leu Leu Phe Trp Ile Phe Ile Lys
1               5                   10


<210> SEQ ID NO 49
<211> LENGTH: 7
<212> TYPE: PRT
<213> ORGANISM: Artificial Sequence
<220> FEATURE:
<223> OTHER INFORMATION: MQP-91

<400> SEQUENCE: 49

Gln Met Val Ser Met Val Gly
1               5


<210> SEQ ID NO 50
<211> LENGTH: 12
<212> TYPE: PRT
<213> ORGANISM: Artificial Sequence
<220> FEATURE:
<223> OTHER INFORMATION: MQP-T234

<400> SEQUENCE: 50

Lys Val Gly Asp Arg Ala Arg Trp Gly Ser Arg Ser
1               5                   10


<210> SEQ ID NO 51
<211> LENGTH: 10
<212> TYPE: PRT
<213> ORGANISM: Artificial Sequence
<220> FEATURE:
```

<223> OTHER INFORMATION: MQP-S442

<400> SEQUENCE: 51

```
Leu Glu Arg Gln Ser Arg Ser Trp Arg Asn
1               5                   10
```

<210> SEQ ID NO 52
<211> LENGTH: 10
<212> TYPE: PRT
<213> ORGANISM: Artificial Sequence
<220> FEATURE:
<223> OTHER INFORMATION: MQP-341

<400> SEQUENCE: 52

```
Glu Trp Leu Gly Arg Gly Arg Phe Asn Gly
1               5                   10
```

<210> SEQ ID NO 53
<211> LENGTH: 10
<212> TYPE: PRT
<213> ORGANISM: Artificial Sequence
<220> FEATURE:
<223> OTHER INFORMATION: MQP-Y9A1

<400> SEQUENCE: 53

```
Ala Arg Leu Leu Phe Trp Ile Phe Ile Lys
1               5                   10
```

<210> SEQ ID NO 54
<211> LENGTH: 10
<212> TYPE: PRT
<213> ORGANISM: Artificial Sequence
<220> FEATURE:
<223> OTHER INFORMATION: MQP-Y9A2

<400> SEQUENCE: 54

```
Lys Ala Leu Leu Phe Trp Ile Phe Ile Lys
1               5                   10
```

<210> SEQ ID NO 55
<211> LENGTH: 10
<212> TYPE: PRT
<213> ORGANISM: Artificial Sequence
<220> FEATURE:
<223> OTHER INFORMATION: MQP-Y9A3

<400> SEQUENCE: 55

```
Lys Arg Ala Leu Phe Trp Ile Phe Ile Lys
1               5                   10
```

<210> SEQ ID NO 56
<211> LENGTH: 10
<212> TYPE: PRT
<213> ORGANISM: Artificial Sequence
<220> FEATURE:
<223> OTHER INFORMATION: MQP-Y9A4

<400> SEQUENCE: 56

```
Lys Arg Leu Ala Phe Trp Ile Phe Ile Lys
1               5                   10
```

<210> SEQ ID NO 57
<211> LENGTH: 10
<212> TYPE: PRT
<213> ORGANISM: Artificial Sequence
<220> FEATURE:
<223> OTHER INFORMATION: MQP-Y9A5

<400> SEQUENCE: 57

Lys Arg Leu Leu Ala Trp Ile Phe Ile Lys
1 5 10

<210> SEQ ID NO 58
<211> LENGTH: 10
<212> TYPE: PRT
<213> ORGANISM: Artificial Sequence
<220> FEATURE:
<223> OTHER INFORMATION: MQP-Y9A6

<400> SEQUENCE: 58

Lys Arg Leu Leu Phe Ala Ile Phe Ile Lys
1 5 10

<210> SEQ ID NO 59
<211> LENGTH: 10
<212> TYPE: PRT
<213> ORGANISM: Artificial Sequence
<220> FEATURE:
<223> OTHER INFORMATION: MQP-Y9A7

<400> SEQUENCE: 59

Lys Arg Leu Leu Phe Trp Ala Phe Ile Lys
1 5 10

<210> SEQ ID NO 60
<211> LENGTH: 10
<212> TYPE: PRT
<213> ORGANISM: Artificial Sequence
<220> FEATURE:
<223> OTHER INFORMATION: MQP-Y9A8

<400> SEQUENCE: 60

Lys Arg Leu Leu Phe Trp Ile Ala Ile Lys
1 5 10

<210> SEQ ID NO 61
<211> LENGTH: 10
<212> TYPE: PRT
<213> ORGANISM: Artificial Sequence
<220> FEATURE:
<223> OTHER INFORMATION: MQP-Y9A9

<400> SEQUENCE: 61

Lys Arg Leu Leu Phe Trp Ile Phe Ala Lys
1 5 10

<210> SEQ ID NO 62
<211> LENGTH: 10
<212> TYPE: PRT
<213> ORGANISM: Artificial Sequence
<220> FEATURE:
<223> OTHER INFORMATION: MQP-Y9A10

<400> SEQUENCE: 62

Lys Arg Leu Leu Phe Trp Ile Phe Ile Ala
1 5 10

<210> SEQ ID NO 63
<211> LENGTH: 9
<212> TYPE: PRT
<213> ORGANISM: Artificial Sequence
<220> FEATURE:
<223> OTHER INFORMATION: MQP-37S1A -continued

```
<400> SEQUENCE: 63

Ala Leu Val Leu Ala Ala Ala Arg Trp
1               5
```